United States Patent [19]

Dennis et al.

[11] Patent Number: 5,976,893
[45] Date of Patent: Nov. 2, 1999

[54] METHODS FOR IDENTIFYING BINDING PARTNERS, AGONISTS, AND ANTAGONIST OF A SERINE/THREONINE TYROSINE KINASE

[75] Inventors: James W. Dennis, Etobicoke; Mike Heffernan; Carol Fode, both of Toronto, all of Canada

[73] Assignee: Mount Sinai Hospital, Toronto, Canada

[21] Appl. No.: 08/834,108

[22] Filed: Apr. 14, 1997

Related U.S. Application Data

[63] Continuation of application No. 08/252,995, Jun. 2, 1994, Pat. No. 5,650,501.

[51] Int. Cl.$^6$ .............................. C12Q 1/48; C12Q 1/00
[52] U.S. Cl. .............................. 436/501; 435/4; 435/194
[58] Field of Search .............................. 436/501; 435/4, 435/194

[56] References Cited

U.S. PATENT DOCUMENTS 5,451,518   9/1995   Kolesnick .............................. 435/194

OTHER PUBLICATIONS

Llamazares, S. et al., Genes & Dev. 5:2153–2165, 1991.
Kitada, K. et al., Mol. and Cell. Biol. 13(7):4445–4457, 1993.
Fenton, B. & Glover, D. M., Nature 363:637–640, 1993.
Sharon, G. & Simchen, G., Genet. 125:475–485, 1990.
Schild, D. & Byers, B., Genet. 96:859–876, 1980.
Simmons, D. L. et al., Mol. and Cell. Biol. 12(9):4164–4169, 1992.
Clay, F. J. et al., Proc. Natl. Acad. Sci. USA 90:4882–4886, 1993.
van den Heuvel, S. and Harlow E., Science 262:2050–2054, 1993.
Dennis, J. W. (1986) Cancer Res. 46:4594–4600.
Heffernan, M. & Dennis, J. W. (1991) Nucleic Acids Research 19(1):85–92.
Padgett, R. A., et al., Ann. Rev. Biochem. 55, 1119–1150, 1986.
Kozak, M. (1986) Cell 44:283–292.
Shaw, G. & Kamen, R. (1986) Cell 46:659–667.
Hanks, S. K. & Quinn, A. M. (1991) Methods. Enzymol. 200:38–63.
Rogers, S., Wells, R. & Rechsteiner, M. (1986) Science 234:364–368.
Stein, R., Mori, N., Matthews, K., Lo, L. C. & Anderson, D. J. (1988) Neuron 1, 463–476.
Hamanaka et al., Cell Growth Diff. 5:249–257, Mar. 1994.
Kruger et al., J. Neuroscience, 11(8):2303, Aug. 1991.
Golsteyn et al., J. Cell Sci., 107:1509–1577, Jun., 1994.

*Primary Examiner*—Elizabeth Kemmerer

[57] ABSTRACT

A serine/theonine kinase protein which is associated with mitotic and meiotic cell division and which is characterized by having a kinase domain in its N-terminus and three PEST regions in the C-terminus, and nucleic acid molecules encoding the protein. Diagnostic and therapeutic methods using the serine/threonine kinase protein and nucleic acid molecules are also described.

4 Claims, 25 Drawing Sheets

FIG. 2

```
   1 GCGGGAATTTTTCAAAATGGGAGCTCCGGGGCGCCGCCCAGGCCTCGGGAGGTACCGGGGGTACCTTTCGGTGGCGTTGGCGGCGTCGCC    90
  91 AGCGGCGGCGTAGAGAAGGCGTCCTGATGGGCGCCAAGACCTGCTGGCTTCTCGGAGCGCTGCCTCGGAGGGGACTGCGAGAAGGCCGAG   180
 181 CCCCGGGCGCCGGCGGCTCGGGAACATGGCGGCGTGCATCGGGGAGAGGATCGAGGACTTTAAGGTTGGAAATCTACTCGGTAAAGGATC   270
   1                 M  A  A  C  I  G  E  R  I  E  D  F  K  V  G  N  L  L  G  K  G  S             22
 271 ATTTGCTGGTGTCTACAGAGCTGAGTCCATACACACTGGTTTGGAAGTTGCAATCAAAATGATAGATAAGAAAGCCATGTACAAAGCTGG   360
  23  F  A  G  V  Y  R  A  E  S  I  H  T  G  L  E  V  A  I  K  M  I  D  K  K  A  M  Y  K  A  G    52
 361 AATGGTACAGAGAGTCCAAAATGAGGTGAAAATACATTGCCAGTTGAAACACCCCTCTGTCTTGGAGCTCTATAATTACTTTGAAGATAA   450
  53  M  V  Q  R  V  Q  N  E  V  K  I  H  C  Q  L  K  H  P  S  V  L  E  L  Y  N  Y  F  E  D  N    82
 451 CAATTATGTCTACCTGGTATTGGAAATGTGCCACAATGGAGAAATGAACAGATATCTGAAGAACAGAATGAAGCCTTTCTCAGAAAGGGA   540
  83  N  Y  V  Y  L  V  L  E  M  C  H  N  G  E  M  N  R  Y  L  K  N  R  M  K  P  F  S  E  R  E   112
 541 AGCTAGGCACTTCATGCACCAGATTATCACAGGAATGTTATATCTTCATTCTCATGGCATATTGCACCGGGACCTCACACTCTCTAACAT   630
 113  A  R  H  F  M  H  Q  I  I  T  G  M  L  Y  L  H  S  H  G  I  L  H  R  D  L  T  L  S  N  I   142
 631 CTTACTTACGCGGAATATGAACATAAAAATTGCTGACTTTGGACTAGCAACGCAGTTGAATATGCCACATGAAAAGCACTATACACTCTG   720
 143  L  L  T  R  N  M  N  I  K  I  A  D  F  G  L  A  T  Q  L  N  M  P  H  E  K  H  Y  T  L  C   172
 721 TGGGACTCCTAATTATATTTCACCAGAAATTGCAACTCGAAGTGCACATGGACTTGAATCTGATATTTGGTCATTGGGCTGTATGTCTTA   810
 173  G  T  P  N  Y  I  S  P  E  I  A  T  R  S  A  H  G  L  E  S  D  I  W  S  L  G  C  M  S  Y   202
 811 TACGTTACTTATTGGAAGACCACCTTTTGACACTGACACAGTCAAGAACACATTGAACAAAGTAGTCCTGGCAGATTATGAAATGCCAGC   900
 203  T  L  L  I  G  R  P  P  F  D  T  D  T  V  K  N  T  L  N  K  V  V  L  A  D  Y  E  M  P  A   232
 901 CTTTTTGTCACGAGAGGCCCAGGACCTTATCCACCCAGTTACTTCGTAGAAACCCTGCAGATCGGTTAAGTCTGTCTTCTGTGTTGGACCA   990
 233  F  L  S  R  E  A  Q  D  L  I  H  Q  L  L  R  R  N  P  A  D  R  L  S  L  S  S  V  L  D  H   262
 991 TCCTTTCATGTCACGAAATCCTTCACCAAAGAGTAAAGACGTAGGGACTGTAGAGGACTCAATGGATAGTGGGCATGCTACACTTTCCAC  1080
 263  P  F  M  S  R  N  P  S  P  K  S |K  D  V  G  T  V  E  D  S  M  D  S  G |H| A  T  L  S  T   292
1081 AACAATTACAGCCTCTTCTGGTACCCAGTTTGAGTGGCAGCCTACTTGACAGAAGACTTTTGGTTGTCAACCACTTCCAAATAAAATTAC  1170
 293  T  I  T  A  S  S  G  T  S  L  S  G  S  L  L  D  R| L  L  V  G  Q  P  L  P  N  K  I  T     322
1171 TGTATTTCAAAAAATAAAAATTCAAGTGACTTTCTTCAGGAGATGGAAGTAATTTTGTACTCAATGGGGAAATCCAGAACAAGAAGC     1260
 323  V  F  Q  K  N  K  N  S  S  D  F  S  S  G  D  G  S  N  F  C  T  Q  W  G  N  P  E  Q  E  A   352
1261 TAATAGTAGGGCACGGGGGAGAGTGATTGAAGATGCAGAAGAGGCCGCATTCTCGATACCTGCGCAGAGCTCATTCCTCTGATAGAGC     1350
 353  N  S  R  G  R  G  R  V  I  E  D  A  E  E  R  P  H  S  R  Y  L  R  R  A  H  S  S  D  R  A   382
1351 CAGCCCCTCTAATCAGTCTCGAGCAAAAACATACTCAGTAGAACGTTGTCACTCAGTAGAAATGCTTTCAAAGCCTAGAAGATCACTGGA  1440
 383  S  P  S  N  Q  S  R  A  K  T  Y  S  V  E  R  C  H  S  V  E  M  L  S  K  P  R  R  S  L  D   412
1441 TGAAAATCAACACAGTTCCAATCATCATTGTCTAGGAAAAACTCCTTTTCCATTTGCAGACCAGACACCTCAGATGGAAATGGTACAGCA  1530
 413  E  N  Q  H  S  S  N  H  H  C  L  G  K  T  P  F  P  F  A  D  Q  T  P  Q  M  E  M  V  Q  Q   442
1531 GTGGTTTGGGAATCTGCAAATGAATGCTCATTTAGGAGAAACTAATGAGCACCACACCGTTAGCCCAAACAGAGATTTCCAGGACTATCC  1620
 443  W  F  G  N  L  Q  M  N  A  H  L  G  E  T  N  E  H  H  T  V  S  P  N  R  D  F  Q  D  Y  P   472
1621 AGATTTGCAGGACACGTTACGAAACGCTTGGACTGACACGAGAGCCAGCAAGAATGCTGATACTTCTGCCAATGTTCATGCTGTAAAGCA  1710
 473  D  L  Q  D  T  L  R  N  A  W  T  D  T  R  A  S  K  N  A  D  T  S  A  N  V  H  A  V  K  Q   502
1711 GCTGAGTGCCATGAAATACATGAGTGCACATCACCATAAGCCTGAGGTCATGCCACAGGAGCCGGGCCTACATCCTCATTCTGAACAAAG  1800
 503  L  S  A  M  K  Y  M  S  A  H  H  H  K  P  E  V  M  P  Q  E  P  G  L  H  P  H  S  E  Q  S   532
1801 CAAGAATAGAAGTATGGAGTCGACACTGGGTTACCAGAAACCTACCTTAAGAAGTATTACATCTCCTCTGATTGCTCACAGATTAAAGCC  1890
 533  K  N  R  S  M  E  S  T  L  G  Y  Q  K  P  T  L  S  S  I  T  S  P  L  I  A  H  R  L  K  P   562
1891 AATCAGACAGAAAACCAAAAAGGCTGTGGTGAGCATCCTTGATTCAGAGGAGGTGTGTGTGGAGCTTCTGAGAGAGTGTGCGTCTGAAGG  1980
 563  I  R  Q  K  T  K  K  A  V  V  S  I  L  D  S  E  E  V  C  V  E  L  L  R  E  C  A  S  E  G   592
1981 ATATGTGAAAGAAGTGCTTCAGATATCCAGTGATGGACTATGATCACTGTTTATTACCCGAACGATGGAAGAGGCTTTCCTCTTGCTGA  2070
 593  Y  V  K  E  V  L  Q  I  S  S  D  G  T  M  I  T  V  Y  Y  P  N  D  G  R  G  F  P  L  A  D   622
2071 CAGACCTCCCTTGCCTACTGACAACATCAGTAGGTACAGCTTTGACAATCTACCAGAAAAATACTGGCGGAAATATCAGTATGCTTCCAG  2160
 623  R  P  P  L  P  T  D  N  I  S  R  Y  S  F  D  N  L  P  E  K  Y  W  R  K  Y  Q  Y  A  S  R   652
2161 ATTCATTCAGCTAGTAAGATCTAAAACTCCCAAAATCACTTATTTTACAAGATATGCTAAATGTATTTTGATGGAAAATTCTCCTGGTGC  2250
 653  F  I  Q  L  V  R  S  K  T  P  K  I  T  Y  F  T  R  Y  A  K  C  I  L  M  E  N  S  P  G  A   682
2251 TGATTTCGAAGTTTGGTTTTATGATGGAGCCAAAATACATAAAACTGAAAATTTAATTCACATAATTGAGAAAACAGGGATATCTTATAA  2340
 683  D  F  E  V  W  F  Y  D  G  A  K  I  H  K  T  E  N  L  I  H  I  I  E  K  T  G  I  S  Y  N   712
2341 TTTAAAAAATGAAAATGAAGTTACCAGCCTGAAAGAGGAAGTAAAAGTATATATGGACCATGCTAATGAGGGTCACCGTATTTGCTTGTC  2430
 713  L  K  N  E  N  E  V  T  S  L  K  E  E  V  K  V  Y  M  D  H  A  N  E  G  H  R  I  C  L  S   742
2431 ACTGGAATCTGTAATCTCTGAGGAGGAAAAGAGAAGCAGGGGTTCTTCATTCTTCCCTATAATCGTAGGAAGAAAACCTGGTAATACTAG  2520
 743  L  E  S  V  I  S  E  E  E  K  R  S  R  G  S  S  F  F  P  I  I  V  G |R  K  P  G  N  T  S   772
2521 TTCACCTAAAGCCTTATCGCCTCCTCCTGTGGACCCAAGCTGCTGTAAGGGAGAGCAGGCGTCAGCAAGCAGCATCGAGCGTGAATAGTGC  2610
 773  S  P |K  A  L  S  A  P  P  V  D  P  S  C  C  K| G  E  Q  A  S  A  S |R  L  S  V  N  S  A   802
2611 CGCTTTCCCCACACAGTCCCCAGGACTCAGTCCTTCCACTGTGACAGTTGAAGGACTTGGCCACACAGCGACTGCCACAGGAACAGGCGT  2700
 803  A  F  P  T  Q  S  P  G  L  S  P  S  T  V  T  Y  E  G  L  G |H| T  A  T  A  T  G  T  G  V   832
2701 CTCTTCAAGTCTTCCTAAATCTGCACAGCTTTTGAAATCTGTTTTTGTGAAAAATGTTGGTTGGGCTACACAGCTAACTAGCGGAGCTGT  2790
 833  S  S  S  L  P  K| S  A  Q  L  L  K  S  V  F  V  K  N  V  G  W  A  T  Q  L  T  S  G  A  Y   862
2791 GTGGGTTCAGTTTAATGATGGGTCACAGTTGGTTGTCAGGCAGGAGTATCTTCCATCAGTTACACATCACCAGATGGTCAGACAACTAG  2880
 863  W  V  Q  F  N  D  G  S  Q  L  V  V  Q  A  G  V  S  S  I  S  Y  T  S  P  D  G  Q  T  T  R   892
2881 GTATGGAGAAAATGAAAAATTACCTGAATACATCAAACAGAAATTACAGTGTCTTTCTTCCATCCTTCTGATGTTTCTAATCCAACTCC  2970
 893  Y  G  E  N  E  K  L  P  E  Y  I  K  Q  K  L  Q  C  L  S  S  I  L  L  M  F  S  N  P  T  P   922
2971 TAATTTTCAGTAATTTAAGTCTCAGAAGTCTATATTTAATAAATGACTTTTTGGCTGGCTTTCAAGTAAGTGATTTTTTAAATTTACTTT  3060
 923  N  F  Q  *                                                                                  925
3061 AACTTCAGAAAGCCTTTCTATTAAACAGAATTTTAATATACACAATAAAAATATAATAAGAAAACAATAAAATTTCAGTTACCTAATATA  3150
3151 GTGGTCATAAGCCTAGGACATCTAATTTTGCTCCAAGCATGTAATCCTTCAAAGTTTGTGCTCCTATGTTTGTATTGAACTAAGTTGTGT  3240
3241 ATGGCTTGTTTGTTTTTGTTATTTTCTTTACTAATAAGACATTGAGAATCACCGACAAAACATAGTTTTCAATTTTTGAATGTGTAAATA  3330
3331 ATGTATTATAAGCAATATGTAAATGTGTATATTTTATATTTATTTTTATAGCACTTGTGTCTGATAACATTTCTGCAAATACATTTTATA  3420
3421 AAATAAACACAGTGGTAAGTTTTCCTT  3447
```

FIG. 3

```
1454  AGGTATTCACCCACCAAAAGCAATGTCAATGTTTTAACTTCATTAAACACCAAACAGCCAATAGTTAAGGATCTTTTGAAAGACCGTATA  1543
 417    R  Y  S  P  T  K  S  N  V  N  V  L  T  S  L  N  T  K  Q  P  I  V  K  D  L  L  K  D  R  I     446
1544  ATGACTGAGCAGTATAAGGATAATCTTTTAAACTTATTGAACAAGTTTGATCGCTAA  1600
 447    M  T  E  Q  Y  K  D  N  L  L  N  L  L  N  K  F  D  R  *     465
```

FIG. 4

```
Sak   IGERTEDFKVGNL......GVYRAESIHTGLEV....IDKAMYEAGMVQRVQ...VK..CO.K..PSVLE  74
Polo  INQR-KTIKRMRF.......EYEIIBVETQDVF....YSKKLMIHHQKE.TAG..T...S..PNIYK      87
Snk   OPTTGKRICMGKVI......EYENTDLTNNKYV...IIPHSRVA.PHQRE.IDK..EL.L..KHV.Q     141
Cdc5  IKTRGKDIH.GHFI......REFQIKD-QSGEIF....TVA.ASIKSEKTR.LLS..Q..KSM..PNI.Q  144
Plk   QPRSRRQ.I.GRFI......KEFEIS.ADTKEVF....IVP.SLLL.PHQKE.MSM..I..RS..NHV.G  115
        I                   II                III Sak   LYNF...NNYVTLV......NGEMNRYL....KPFS....IFMN...TPN..SHG.I.........TLL  144
Polo  RHNY...SONIVIV......KRSMMELG..--ST....YYTTT..IQGVF..DNRI..........EL  156
Snk   FYHF...KENIVIL......SRRSNAHIL...V-L....YTLR.VSRL..EOEI..R.........FTI 210
Cdc5  EIDC...ROSNYVIL.....PNGSLMELL...V-L....RFTTT..LGAIK..SRRV.........IFF 213
Plk   BHOF...SDFYVV.......RRRSLLELH..R.A-L...YYLR.VLR.C..NNQV..I.........LL 184
        IV          V         VIa         VIb Sak   TRMM..I.........OLNMPHEKH.....ATRSANG-..............  212
Polo  NDLLH..V..DLAT..RIEYEGERKK..ST.A.I..A..ETKKGHS-..............  224
Snk   NEAMEL.V....QLA.ARLEPLEHRR....E.T.P..S..VENKOGHG-..............  278
Cdc5  DSNYN..I....GLA.VLANESERK.....E.T.P..A..VEMGKHSGHSF..........  283
Plk   NEDLEV..I....GLA.TKVEYEGERKK..T.A...I...LSKKGH--SF............  252
        VII          VIII            IX Sak   TDTVKNTLNKVVLADTE.....--AFLSREAQD..IHQL..RN.AD..SLSSVLDHP.MSRNPS..SKDVG  277
Polo  TKTLKDTYSKEKKCE.R.....--YLRKPAADMVIAM..OPN.ES..PAIGQLLNF..LKGSKV..FLPSS  289
Snk   TTNLKETIRCIREARY.....--SLLAPKHE.ASM..SK.EI..SLDDI.RHO.FLQGFT..DRLSSS   343
Cdc5  ARDVNTIYER.KCRDFS.....RDKPISDEGKI.RDI.S-D.I...SLTEIMDYVWFRGTFP..SIPSTV  349
Plk   TSCLKETYLR.KKNE.S.....--KHINPVAAS..QKM..TO.TA..TIHELLNDE.FTSGY..ARLPIT  317
        X                    XI
```

METHODS FOR IDENTIFYING BINDING PARTNERS, AGONISTS, AND ANTAGONIST OF A SERINE/THREONINE TYROSINE KINASE

This application is a continuation of application Ser. No. 08/252,995, filed Jun. 2, 1994, now U.S. Pat. No. 5,650,501.

FIELD OF THE INVENTION

The invention relates to a novel serine/threonine kinase protein and isoforms and parts thereof, nucleic acid molecules encoding the novel protein and fragments thereof, and uses of the protein and nucleic acid molecules.

BACKGROUND OF THE INVENTION

The *Drosophila polo* and *Saccharomyces cerevisiae* CDC5 genes encode serine/threonine kinases which are highly related in sequence (47% identity in the catalytic domain) and in function (Llamazares, S. et al., (1991) Genes Dev. 5,2153–2165, and Kitada, K. et al, (1993) Mol. Cell. Biol. 13, 4445–4457). Phenotypic analysis of mutant alleles of polo and CDC5 indicates that both are required for the proper formation and function of the spindle during mitotic and meiotic cell divisions (Llamazares, S. et al., (1991) Genes Dev. 5, 2153–2165, 1991; Fenton, B. & Glover, D. M. (1993) Nature 363, 637–640; Sharon, G. & Simchen, G. (1990) Genet. 125, 475–485; Schild, D. & Byers, B. (1980) Genet. 96, 859–876). Two related murine genes, snk (Simmons, D. L., Neel, B. G., Stevens, R., Evett, G. & Erikson, R. L. (1992) *Mol. and Cell. Biol.* 12, 4164–4169) and plk (Clay, F. J., McEwen, S. J., Bertoncello, I., Wilks, A. F. & Dunn, A. R. (1993) *Proc. Natl. Acad. Sci.* USA 90, 4882–4886) have recently been cloned and may also play a role in regulating cell proliferation based on cell cycle dependent changes in their transcription levels and a correlation between the tissue specific pattern of plk expression and active cell division.

SUMMARY OF THE INVENTION

The present inventors have identified and characterized a serine/threonine kinase protein that plays an important role in cell proliferation. In particular, the present inventors isolated murine cDNAs encoding isoforms of a serine/threonine kinase, designated Sak. The isoforms, Sak-a and Sak-b, differ in their non-catalytic C-terminal ends. Sak is related to members of the polo subfamily of kinase. Sak has a kinase domain in the N-terminal region (See FIG. 1) and the sequence in the N-terminal region has significant homology to the polo subfamily. The sak kinase domain also diverges significantly from other members of the polo subfamily. Within subdomain VI-B, the threonine residue in the sak sequence DLTLSN is in a position normally occupied by a lysine, not only in proteins within the polo subfamily, but in the majority of serine/threonine kinases. The serine residue in this sequence is replaced by a glycine in all other members of the polo subfamily. A 30 amino acid homology domain identified in the C-terminus of the polo, CDC5, plk and snk kinases is absent in both of the sak proteins (Clay, F. J., McEwen, S. J., Bertoncello, I., Wilks, A. P. & Dunn, A. R. (1993) *Proc.-b Natl. Acad. Sci.* USA 90, 4882–4886). Three PEST regions, each containing 2 sequences in tandem in Sak-a and one in Sak-b, were also identified in the C-terminal region of the proteins.

Northern and in situ RNA analyses of sak expression in mouse embryos and adult tissues revealed that expression is associated with mitotic and meiotic cell division. In addition, during embryogenesis, sak expression is prominent in the respiratory and olfactory mucosa. The pattern of sak expression and its sequence homology with the polo gene family indicate that sak may play a role in cell proliferation. In support of this, the present inventors found that cell growth was suppressed by expression of a sak-a antisense fragment in CHO cells.

The present invention therefore provides a purified and isolated nucleic acid molecule containing a sequence encoding a serine/threonine kinase protein which is associated with mitotic and meiotic cell division and which is characterized by having a kinase domain in its N-terminus and three PEST regions in the C-terminus, or an oligonucleotide fragment of the sequence which is unique to the serine/threonine kinase protein.

The kinase protein of the invention is also referred to herein as Sak for Snk/Plk-akin kinase and the gene encoding the protein is referred to herein as sak.

In an embodiment of the invention, the purified and isolated nucleic acid molecule comprises (a) a nucleic acid sequence encoding a protein having the amino acid sequence from amino acids 5 to 277 as shown in SEQ ID NO:2; (b) nucleic acid sequences complementary to (a); (c) nucleic acid sequences encoding a protein having at least 43% identity to (a); or, (d) a fragment of (a) or (b) that is at least 15 bases and which will hybridize to (a) or (b) under stringent hybridization conditions.

Preferably, the purified and isolated nucleic acid molecule comprises (a) a nucleic acid sequence corresponding to nucleic acids 218 to 1036 as shown in SEQ ID NO:1, wherein T can also be U;

(b) nucleic acid sequences complementary to (a);

(c) nucleic acid sequences which are at least 56% identical to (a); or, (d) a fragment of (a) or (b) that is at least 15 bases and which will hybridize to (a) or (b) under stringent hybridization conditions.

In another embodiment of the invention, the purified and isolated nucleic acid molecule comprises (a) a nucleic acid sequence encoding a protein having the amino acid sequence as shown in SEQ ID NO:2;

(b) nucleic acid sequences complementary to (a);

(c) nucleic acid sequences encoding a protein having at least 43% identity to (a); or, (d) a fragment of (a) or (b) that is at least 15 bases and which will hybridize to (a) or (b) under stringent hybridization conditions.

Most preferably, the purified and isolated nucleic acid molecule comprises (a) a nucleic acid sequence as shown in SEQ ID NO:1, wherein T can also be U;

(b) nucleic acid sequences complementary to (a);

(c) nucleic acid sequences which are at least 56% identical to (a); or, (d) a fragment of (a) or (b) that is at least 15 bases and which will hybridize to (a) or (b) under stringent hybridization conditions.

In a further embodiment of the invention, the purified and isolated nucleic acid molecule comprises (a) a nucleic acid sequence encoding a protein having the amino acid sequence as shown in SEQ ID NO:4; (b) nucleic acid sequences complementary to (a); (c) nucleic acid sequences encoding proteins having at least 43% identity with amino acids 5 to 277 in SEQ ID NO:4; or, (d) a fragment of (a) or (b) that is at least 15 bases and which will hybridize to (a) or (b) under stringent hybridization conditions. Preferably, the purified and isolated nucleic acid molecule comprises (a) a nucleic acid sequence as shown in SEQ ID NO:3, wherein T can also be U; (b) nucleic acid sequences complementary to (a); (c) nucleic acid sequences having at least 56% identity to nucleotides 218 to 1036 in SEQ ID NO: 3; or, (d) a fragment of (a) or (b) that is at least 15 bases and which will hybridize to (a) or (b) under stringent hybridization conditions.

In a still further embodiment of the invention, the purified and isolated nucleic acid molecule comprises (a) a nucleic acid sequence encoding a protein having the amino acid sequence as shown in SEQ ID NO:6; (b) nucleic acid sequences complementary to (a); (c) nucleic acid sequences encoding a protein having at least 43% identity with amino acids 218 to 1036 in SEQ. ID. NO:6; or, (d) a fragment of (a) or (b) that is at least 15 bases and which will hybridize to (a) or (b) under stringent hybridization conditions. Preferably, the purified and isolated nucleic acid molecule comprises (a) a nucleic acid sequence as shown in SEQ ID NO:5, wherein T can also be U; (b) nucleic acid sequences complementary to (a); (c) nucleic acid sequences having at least 56% identity with nucleotides 218 to 1036 of SEQ ID NO:5; or, (d) a fragment of (a) or (b) that is at least 15 bases and which will hybridize to (a) or (b) under stringent hybridization conditions.

It is contemplated that a nucleic acid molecule of the invention may be prepared having deletion and insertion mutations. For example, the kinase domain or parts thereof may be deleted.

The invention further contemplates a purified and isolated double stranded nucleic acid molecule containing a nucleic acid molecule of the invention or a fragment thereof, hydrogen bonded to a complementary nucleic acid base sequence.

The nucleic acid molecules of the invention, or fragments thereof may be inserted into an appropriate expression vector, i.e. a vector which contains the necessary elements for the transcription and translation of the inserted protein-coding sequence. Accordingly, recombinant DNA molecules adapted for transformation of a host cell may be constructed which comprise a nucleic acid molecule of the invention and one or more transcription and translation elements operatively linked to the nucleic acid molecule.

In an embodiment of the invention, a recombinant molecule is provided which contains a nucleic acid molecule of the invention having a deletion or insertion mutation. Such a recombinant molecule may further comprise a reporter gene.

The recombinant molecule can be used to prepare transformed host cells expressing the protein or part thereof encoded by a nucleic acid molecule of the invention. Therefore, the invention further provides host cells containing a recombinant molecule of the invention. The invention also contemplates transgenic non-human mammals whose germ cells and somatic cells contain a recombinant molecule of the invention.

The invention further provides a method for preparing a novel serine/threonine kinase protein or isoforms or parts thereof utilizing the purified and isolated nucleic acid molecules of the invention.

The invention further broadly contemplates a purified and isolated serine/threonine kinase protein which is associated with mitotic and meiotic cell division and which is characterized by having a kinase domain in its N-terminus and three PEST regions in the C-terminus, or an isoform or part of the protein. In a preferred embodiment, a purified serine/threonine kinase protein is provided which has the amino acid sequence as shown in SEQ ID NO:2, SEQ. ID. NO:4 or SEQ. ID. NO:6, or a sequence having at least 43% identity with amino acids 5 to 277 in SEQ ID NO:2, SEQ. ID. NO:4 or SEQ. ID. NO:6. The serine/threonine kinase protein of the invention may also be catalytically activated through binding to positive and/or negative regulators.

The kinase protein of the invention, or isoforms or parts thereof, may be conjugated with other molecules, such as proteins or polypeptides. This may be accomplished, for example, by the synthesis of N-terminal or C-terminal fusion proteins. In a preferred embodiment a fusion protein is provided comprising a part of the protein of the invention, preferably the kinase domain, or sequences having at least 43% identity thereto.

The invention also permits the construction of nucleotide probes which are unique to the nucleic acid molecules of the invention and accordingly to the novel serine/threonine kinase protein of the invention or an isoform, or part of the protein. Thus, the invention also relates to a probe comprising a nucleotide sequence coding for a protein which displays the properties of the novel serine threonine kinase of the invention or a part which is unique to the protein. The probe may be labelled, for example, with a detectable substance and it may be used to select from a mixture of nucleotide sequences a nucleotide sequence coding for a protein which displays the properties of the novel serine/threonine kinase protein of the invention, or a part thereof.

The invention further provides a method for identifying a substance which is capable of binding to the novel serine/threonine kinase protein of the invention, or an isoform or part of the protein, comprising reacting the novel serine/threonine kinase protein of the invention, or isoform or part of the protein, with at least one substance which potentially can bind with the kinase protein, or isoform, or part of the protein, under conditions which permit the formation of substance-kinase protein complexes, and assaying for substance-kinase protein complexes, for free substance, for non-complexed kinase proteins, or for activation of the kinase proteins.

In an embodiment of the method, positive and/or negative regulators of the serine/threonine kinase protein of the invention are identified which are capable of binding to and activating the novel serine/threonine kinase protein of the invention. Regulators which bind to and activate the novel serine/threonine kinase protein of the invention may be identified by assaying for serine/threonine kinase activity.

The invention still further provides a method for identifying a substance which is a substrate of the novel serine/threonine kinase protein of the invention, or an isoform or part of the protein, comprising reacting an activated serine/threonine kinase protein of the invention, or part of the protein, preferably the kinase domain, with at least one substance which potentially is a substrate of the kinase protein, or part of the protein, under conditions which permit the phosphorylation of serine/threonine residues, and assaying for phosphorylation of the substance.

Still further, the invention provides a method for assaying a medium for the presence of an agonist or antagonist of the interaction of a serine/threonine kinase protein of the invention or an isoform or part thereof, and a substance which binds to the serine/threonine kinase protein and activates the kinase protein, or isoform or part thereof, or a substance which is a substrate of the kinase protein. In an embodiment, the method comprises providing a known concentration of a serine/threonine kinase protein of the invention, or an isoform or part of the protein, incubating the kinase protein, isoform or part of the protein with a substance which is a substrate of the kinase protein, or isoform or part of the protein, and a suspected agonist or antagonist substance, under conditions which permit the phosphorylation of the substrate, and assaying for phosphorylation of the substrate. In a second embodiment, the method comprises providing a known concentration of a serine/threonine kinase protein of the invention, or an isoform or part of the protein, incubating the kinase protein with a substance which is capable of binding to and activating the kinase protein, or isoform or part of the protein, and a suspected agonist or antagonist substance under conditions which permit the formation of substance-protein complexes, and assaying for activation of the kinase protein. The methods of the invention permit the identification of potential stimulators or inhibitors of cell proliferation which will be useful in the treatment of proliferative disorders.

The invention further contemplates antibodies having specificity against an epitope of the kinase protein of the invention or an isoform or part of the protein which is unique to the kinase protein. Antibodies may be labelled with a detectable substance and they may be used to detect the novel kinase protein of the invention in tissues and cells. The antibodies may accordingly be used to monitor cell proliferation.

Substances which affect cell proliferation may be identified using the methods of the invention by comparing the pattern and level of expression of the novel kinase protein of the invention in tissues and cells in the presence and in the absence of the substance. Thus, the invention provides a method for screening for substances having pharmaceutical utility in the treatment and diagnosis of proliferative disorders.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 2 shows the nucleotide sequence of the sak-a transcriptional unit and the deduced amino acid sequence (SEQ ID NOS:3 & 6);

FIG. 3 shows the nucleotide and predicted amino acid sequences of the coding region of sak-b, beginning from the AG dinucleotide that marks the point of sequence divergence from sak-a (SEQ ID NOS:5 & 6);

FIG. 4 shows an amino acid alignment of the kinase domains of Sak, *Drosophila polo,* murine plk, murine snk and yeast CDC5 (SEQ ID NOS:10–14);

DETAILED DESCRIPTION OF THE INVENTION

I. Characterization of Nucleic Acid Molecules and Proteins of the Invention

Figure 1:
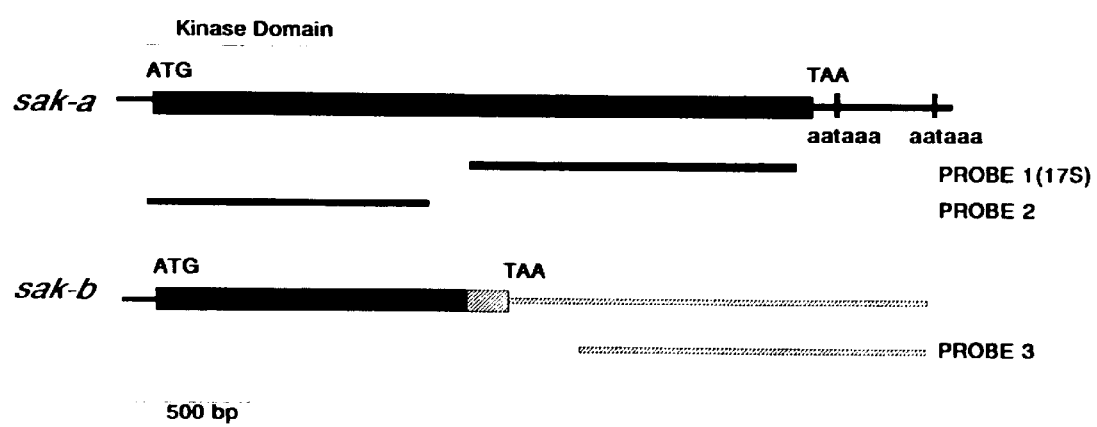
FIG. 1 is a schematic diagram of the sak cDNAs and nucleotide sequence.

As hereinbefore mentioned, the present inventors have identified and sequenced nucleic acid molecules encoding a novel serine/threonine kinase protein. The sak-a and sak-b cDNA appear to represent alternatively spliced forms of the gene given that the sequences diverge after an AG dinucleotide (nt 1456, 1457), a sequence frequently found 5' to splice-donor sites. FIG. 1 shows the open reading frames (black boxes) of the Sak-a and Sak-b transcriptional units which are flanked by ATG start and TAA stop codons. In FIG. 1, the point of sequence divergence is marked in Sak-b by the striped box. The sak-a transcriptional unit encodes a 925 amino acid protein ($M_r$=103 kDa) and the sak-b encoded protein is 464 amino acids in length ($M_r$=53 kDa), with the first 416 amino acids of both proteins being identical but each having different C-terminal tails of 509 (FIG. 2, SEQ ID NO:3) and 48 amino acids (FIG. 3, SEQ ID NO:5), respectively. The N-terminal region common to both sak-a and sak-b proteins has significant homology to the polo subfamily of serine/threonine kinases and they have a common structural organization with the kinase domain located in the N-terminus, followed by a C-terminal domain. The sak kinase domain also diverges significantly from other members of the polo subfamily in subdomain VI-B. Within this subdomain, the threonine residue in the sak sequence DLTLSN (SEQ ID NO:7) is in a position normally occupied by a lysine, not only in proteins within the polo subfamily, but in the majority of serine/threonine kinases. The serine residue in this sequence is replaced by a glycine in all other members of the polo subfamily. Sak also has the sequence GTPNYISPE (SEQ ID NO:8)in subdomain VIII which matches closely with the GTXXYXAPE (SEQ ID NO:9) consensus sequence characteristic of serine/threonine kinases (Hanks, S. K. & Quinn, A. M. (1991) *Methods. Enzymol.* 200, 38–63). A 30 amino acid homology domain identified in the C-terminus of the polo, CDC5, plk and snk kinases is absent in both of the predicted sak proteins (Clay, F. J., McEwen, S. J., Bertoncello, I., Wilks, A. F. & Dunn, A. R. (1993) *Proc. Natl. Acad. Sci.* USA 90, 4882–4886). Three PEST regions, each containing 2 sequences in tandem in Sak-a and one in Sak-b, were identified in the C-terminal region of the proteins. PEST sequences are rich in proline, serine, threonine, aspartate and glutamate residues, and flanked on either side by a basic amino acid.

In accordance with an embodiment of the invention a purified and isolated nucleic acid molecule is provided containing a sequence encoding a protein having the amino acid sequence as shown in SEQ ID NO:2. Most preferably, the purified and isolated nucleic acid molecule of the invention contains a nucleic acid sequence as shown in SEQ ID NO:1. The nucleic acid and amino acid sequences in SEQ.

ID. NO:1 and 2, respectively, represent the nucleic acid and amino acid sequence of the N-terminal region of the Sak-a and Sak-b isoforms.

In accordance with another embodiment of the invention a purified and isolated nucleic acid molecule is provided containing a sequence encoding a protein having the amino acid sequence as shown in SEQ ID NO:4. Most preferably, the purified and isolated nucleic acid molecule of the invention contains a nucleic acid sequence as shown in SEQ ID NO:3. The nucleic acid and amino acid sequences in SEQ. ID. NO:3 and 4, respectively, represent the nucleic acid and amino acid sequences of the Sak-a isoform of the serine/threonine kinase protein of the invention.

In accordance with still another embodiment of the invention a purified and isolated nucleic acid molecule is provided containing a sequence encoding a protein having the amino acid sequence as shown in SEQ ID NO:6. Most preferably, the purified and isolated nucleic acid molecule of the invention contains a nucleic acid sequence as shown in SEQ ID NO:5. The nucleic acid and amino acid sequences in SEQ. ID. NO:5 and 6, respectively, represent the nucleic acid and amino acid sequences of the Sak-b isoform of the serine/threonine kinase protein of the invention.

Fragments of the nucleic acid molecules are contemplated by the present invention. In a preferred embodiment, the fragments include fragments of the nucleotide sequences as shown in SEQ. ID. NO:1, NO:3, and NO:5 and that have at least 15 bases, and which are capable of hybridizing to the nucleotide sequence as shown in SEQ ID NO. 1, NO.3, and No. 5 respectively under stringent hybridization conditions as described herein. These fragments may encode, for example, the kinase domain (amino acids 5 to 277 shown in SEQ ID NO:2, 4 and 6) or the carboxy tail (amino acids 417 to 926 in SEQ ID NO:4, and amino acids 417 to 465 in SEQ ID. NO. 6).

It will also be appreciated that a double stranded nucleotide sequence comprising a nucleic acid molecule of the invention or a fragment thereof, hydrogen bonded to a complementary nucleotide base sequence, and an RNA made by transcription of this double stranded nucleotide sequence are contemplated by the present invention.

Further, it will be appreciated that the invention includes nucleic acid or amino acid sequences which have substantial sequence identity with the nucleic acid and amino acid sequences shown in SEQ ID NOS:1 to 6 and in FIGS. 2 and 3, and fragments thereof. The term "sequences having substantial sequence identity" means those nucleic acid and amino acid sequences which have slight or inconsequential sequence variations from the sequences disclosed in FIGS. 2 and 3 and in SEQ ID NOS: 1 to 6, i.e. the sequences function in substantially the same manner to produce substantially the same polypeptides as the actual sequences. The variations may be attributable to local mutations or structural modifications.

Nucleic acid sequences having substantial identity include nucleic acid sequences which encode proteins having at least 43% sequence identity with the amino acid sequence corresponding to amino acids 5 to 277 as shown in SEQ. ID. NO:2; nucleic acid sequences having at least 56% identity with the nucleic acid sequence corresponding to nucleic acids 218 to 1036 as shown in SEQ. ID. NO.:1; and fragments thereof having at least 15 bases which will hybridize to these sequences under stringent hybridization conditions.

Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor). By way of example only, stringent hybridization with short nucleotides may be carried out at 5°–10° below the $T_m$ using high concentrations of probe such as 0.01–1.0 pmole/ml.

The invention further provides amino acid sequences which have substantial identity with the amino acid sequences shown in SEQ ID NO:2, NO.:4 and NO.:6 and in FIGS. 2 and 3. Substantially identical amino acid sequences include sequences having at least 43% sequence identity in the kinase domain set out in SEQ ID NOS:2, 4 and 6 (amino acids 5 to 277). The invention still further provides peptides which are unique to the serine/threonine kinase protein of the invention. Preferably, the peptides have at least 10 to 20 amino acids. For example the peptides may contain the amino acid sequences of the kinase domain, or subdomains thereof such as subdomain VI-B shown in FIG. 4, or the amino acid sequences of the C-terminal domains of Sak-a and Sak-b.

The nucleic acid sequence contained in the nucleic acid molecules of the invention or a fragment thereof, may be inverted relative to their normal presentation for transcription to produce antisense nucleic acid molecules. The antisense nucleic acid molecules may be constructed using chemical synthesis and enzymatic ligation reactions using procedures known in the art. The antisense nucleic acid molecules of the invention or a fragment of the antisense sequence, preferably containing at least 15 bases, may be chemically synthesized using naturally occurring nucleotides or variously modified nucleotides designed to increase the biological stability of the molecules or to increase the physical stability of the duplex formed with Sak mRNA or the Sak gene e.g. phosphorothioate derivatives and acridine substituted nucleotides. The antisense sequences may be produced biologically using an expression vector introduced into cells in the form of a recombinant plasmid, phagemid or attenuated virus in which antisense sak sequences are produced under the control of a high efficiency regulatory region, the activity of which may be determined by the cell type into which the vector is introduced.

A number of unique restriction sequences for restriction enzymes are incorporated in the nucleic acid sequences identified in SEQ ID NO:1, NO:3 and NO:5 and these provide access to nucleic acid sequences which code for polypeptides unique to the kinase protein of the invention. Nucleic acid sequences unique to the kinase protein of the invention or isoforms or parts thereof, can also be constructed by chemical synthesis and enzymatic ligation reactions carried out by procedures known in the art.

The invention also contemplates forms of the kinase protein which contain the same number and kinds of amino acids as the protein of the invention, but having a different molecular structure and the same functional properties as the novel kinase protein of the invention as described herein.

The present invention also includes fusion proteins containing the kinase protein of the invention, or an isoform, or part thereof. For example, the kinase protein or portions thereof may be conjugated with a selected protein or marker protein to produce fusion proteins.

The present invention also includes a kinase protein of the invention, or an isoform, or part thereof, preferably the kinase domain, which is enzymatically active. The catalytically active form of the protein or isoform or part thereof is also referred to herein as an "activated serine/threonine kinase protein or isoform or part thereof" or "catalytically activated serine/threonine kinase protein or isoform or part thereof".

II. Expression Pattern of the Kinase Protein of the Invention

A detailed study of sak expression by Northern and RNA in situ analyses shows that sak expression correlates with mitotic and meiotic activity in embryonic and adult tissues. For example, sak transcripts in the embryonic CNS are confined to the ventricular zones where neuroblasts are actively dividing and are not detected in the intermediate or marginal zones where the post-mitotic neurons are located. In adult mice, sak is expressed in tissues with a mitotic component, including hematopoietic tissues, the stem cells of the intestinal crypt, the granulosa cells of developing ovarian follicles and in the matrix, or growth region of the hair follicle. RNA in situ analysis revealed high levels of sak transcripts in meiotic spermatocytes and oocytes.

In addition to mitotically dividing cells, the respiratory and olfactory mucosa represent major sites of sak expression during embryogenesis. sak is expressed in the basal region of the olfactory epithelium, consisting mainly of progenitor stem cells for the olfactory neuronal lineage. In the respiratory system, high levels of sak expression are seen in the mucous-secreting and ciliated cells epithelium of the nasal cavity and larger airways, with levels decreasing as the respiratory tract branches.

A common feature of ciliated and dividing cells is the motile nature of the microtubular system. Defects in the organization of the microtubular system during cell division are seen in polo$^1$ homozygotes and CDC5$^{ts}$ mutants, suggesting that this family of kinases including sak, may regulate microtubule-mediated processes.

III. Preparation of Nucleic Acid Molecules and Proteins of the Invention

The nucleic acid molecules of the invention encoding the novel kinase protein, or fragments thereof, may be isolated and sequenced using procedures known in the art. For example, the Sak coding region may be cloned by transfecting a murine lymphoid cDNA library into CHOP cells, treating with the sialic acid binding lectin wheat germ agglutinin (WGA), and isolating WGA resistant CHOP clones containing a 1.5 kb cDNA insert (17S clone, FIG. 1). The 17S partial cDNA fragment, a more 5' fragment (probe 2, FIG. 1) or a probe with sequences unique to the 3 untranslated region of sak-b (probe 3, FIG. 1) may be used to obtain full-length clones from the lymphoid cDNA library. Oligonucleotides specific for the novel serine/threonine kinase protein and which can be used as probes may also be identified by comparing the nucleic acid sequence of the nucleic acid molecules of the invention to know sequences, for example, sequences of the other members of the polo subfamily. Nucleic acid molecules of the present invention encoding the novel kinase protein and oligonucleotide fragments thereof, may also be constructed by chemical synthesis and enzymatic ligation reactions using procedures known in the art.

The novel kinase protein of the invention, or isoforms or parts thereof, may be prepared using recombinant DNA methods. Accordingly, the nucleic acid molecules of the present invention having a sequence which codes for the kinase protein of the invention, or a fragment thereof may be incorporated in a known manner into an appropriate expression vector which ensures good expression of the kinase protein or isoform or part thereof. Possible expression vectors include but are not limited to cosmids, plasmids, or modified viruses, so long as the vector is compatible with the host cell used.

The invention therefore contemplates a recombinant molecule of the invention containing a nucleic acid molecule of the invention, or a fragment thereof, and the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the host cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native kinase protein and/or its flanking regions.

The recombinant molecules of the invention may also contain a reporter gene which facilitates the selection of host cells transformed or transfected with a recombinant molecule of the invention. Examples of reporter genes are genes encoding a protein such as β-galactosidase, chloramphenicol acetyltransferase, firefly luciferase, or an immunoglobulin or portion thereof such as the Fc portion of an immunoglobulin preferably IgG. In a preferred embodiment, the reporter gene is lac Z. Transcription of the reporter gene is monitored by changes in the concentration of the reporter protein such as β-galactosidase, chloramphenicol acetyltransferase, or firefly luciferase. This makes it possible to visualize and assay for expression of recombinant molecules of the invention and in particular to determine the effect of a mutation on expression and phenotype.

Recombinant molecules can be introduced into host cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. Nos. 4,801,542; Upshall et al., 4,935,349; Hagen et al., 4,784, 950; Axel et al., 4,399,216; Goeddel et al., 4,766,075; and Sambrook et al. Molecular Cloning A Laboratory Manual, 2nd edition, Cold Spring Harbor Laboratory Press, 1989, all of which are incorporated herein by reference and see the detailed discussion below).

Suitable host cells include a wide variety of prokaryotic and eukaryotic host cells, including bacterial, mammalian, yeast or other fungi, viral, plant, or insect cells.

More particularly, bacterial host cells suitable for carrying out the present invention include *E. coli, B. subtilis, Salmonella typhimurium,* and various species within the genus' Pseudomonas, Streptomyces, and Staphylococcus, as well as many other bacterial species well known to one of ordinary skill in the art. Representative examples of bacterial host cells include DH5α (Stratagene, LaJolla, Calif.), JM109 ATCC No. 53323, HB101 ATCC No. 33694, and MN294. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, pCDM8, and Bluescript M13 (Stratagene, La Jolla, Calif.).

Yeast and fungi host cells suitable for carrying out the present invention include, among others *Saccharomyces cerevisae,* the genera Pichia or Kluyveromyces and various species of the genus Aspergillus. Suitable expression vectors for yeast and fungi include, among others, YC$_p$50 (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells. Suitable expression vectors for directing expression in mammalian cells generally include a promoter, as well as other transcription and translation control sequences. Common promoters include SV40, MMTV,, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., supra).

Given the teachings provided herein, promoters, terminators, and methods for introducing expression vectors of an appropriate type into plant, avian, and insect cells may also be readily accomplished. For example, within one embodiment, Sak or derivatives thereof may be expressed from plant cells (see Sinkar et al., J. Biosci (Bangalore) 11:47–58, 1987, which reviews the use of Agrobacterium rhizogenes vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Insect cells suitable for carrying out the present invention include cells and cell lines from Bombyx or Spodotera species. Suitable expression vectors for directing expression in insect cells include Baculoviruses such as the *Autographa california* nuclear polyhedrosis, virus (Miller et al. 1987, in *Genetic Engineering,* Vol. 8 ed. Setler, J. K. et al., Plenum Press, New York) and the *Bombyx mori* nuclear polyhedrosis virus (Maeda et al., 1985, Nature 315:592).

Alternatively, the kinase protein of the invention, isoforms or parts thereof may be expressed in non-human transgenic animals such as, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The kinase protein of the invention or isoforms or parts thereof may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

The kinase protein of the invention, or isoforms or parts thereof, may be conjugated with other molecules, such as proteins or polypeptides. This may be accomplished, for example, by the synthesis of N-terminal or C-terminal fusion proteins. Thus, fusion proteins may be prepared by fusing, through recombinant techniques, the N-terminal or C-terminal of the kinase protein or parts thereof, and the sequence of a selected protein or marker protein with a desired biological function. The resultant fusion proteins contain the kinase protein or a portion thereof fused to the selected protein or marker protein as described herein. Examples of proteins which may be used to prepare fusion proteins include immunoglobulins and parts thereof such as the constant region of immunglobulin γ1, and lymphokines such as gamma interferon, tumor necrosis factor, IL-1, IL-2, IL-3, IL-4, IL-5, IL-6, IL-7, IL-8, IL-9, IL-10, IL-11, GM-CSF, CSF-1, G-CSF, hemaglutinin 1, and enzymes such as β-galactosidase, chloramphenicol acetyltransferase, firefly luciferase.

Sequences which encode the above-described proteins may generally be obtained from a variety of sources, including for example, depositories which contain plasmids encoding sequences including the American Type Culture Collection (ATCC, Rockville Md.), and the British Biotechnology Limited (Cowley, Oxford England). Examples of such plasmids include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon,) ATCC Nos. 31902 and 39517 (which contains sequences encoding beta interferon), ATCC No. 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC Nos. 57592 (which contains sequences encoding Interleukin-4). ATCC Nos. 59394 and 59395 (which contain sequences encoding Interleukin-5), and ATCC No. 67153 (which contains sequences encoding Interleukin-6.

Activated serine/threonine kinase proteins of the invention, or isoforms or parts thereof, may be prepared by reacting a serine/threonine kinase protein of the invention or a part thereof with a positive and/or negative regulator which is identified using the methods of the invention described herein.

IV. Utility of the Nucleic Acid Molecules and Proteins of the Invention

The nucleic acid molecules of the invention or fragments thereof, allow those skilled in the art to construct nucleotide probes for use in the detection of nucleotide sequences in biological materials. Examples of probes include the 17S partial cDNA fragment, a more 5' fragment (probe 2, FIG. 1) and a probe with sequences unique to the 3 untranslated region of sak-b (probe 3, FIG. 1). A nucleotide probe may be labelled with a detectable substance such as a radioactive label which provides for an adequate signal and has sufficient half-life such as $^{32}$P, $^{3}$H, $^{14}$C or the like. Other detectable substances which may be used include antigens that are recognized by a specific labelled antibody, fluorescent compounds, enzymelac Zs, antibodies specific for a labelled antigen, and chemiluminescense. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that encode proteins related to or analogous to the kinase protein of the invention. The nucleotide probes may therefore be useful in the diagnosis of proliferative disorders arising from mutations or alterations to the Sak gene or a homologue thereof.

Antisense nucleic acid molecules of the invention may be used in gene therapy to treat or prevent proliferative disorders. For a discussion of the regulation of gene expression using anti-sense genes see Weintraub, H. et al., *Antisense RNA as a molecular tool for genetic analysis,* Reviews—Trends in Genetics, Vol. 1(1) 1986. Recombinant molecules comprising an antisense sequence or oligonucleotide fragment thereof, may be directly introduced into cells of tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The kinase protein of the invention and isoforms and parts thereof, for example amino acids of the carboxy terminal tail, may be used to prepare antibodies. Antibodies having specificity for Sak protein may also be raised from fusion proteins created by expressing Sak fusion proteins in bacteria as described above.

Within the context of the present invention, antibodies are understood to include monoclonal antibodies, polyclonal antibodies, antibody fragments (e.g., Fab, and F(ab')$_2$ and recombinantly produced binding partners. Antibodies are understood to be reactive against Sak protein if they bind with a $K_a$ of greater than or equal to $10^{-7}$M. As will be appreciated by one of ordinary skill in the art, antibodies may be developed which not only bind to Sak protein, but which bind to a regulator of Sak protein, and which also block the biological activity of Sak protein. Such antibodies will be useful in the diagnosis and treatment of proliferative disorders.

Polyclonal antibodies may be readily generated by one of ordinary skill in the art from a variety of warm-blooded animals such as horses, cows, various fowl, rabbits, mice, or rats. Briefly, Sak protein is utilized to immunize the animal through intraperitoneal, intramuscular, intraocular, or subcutaneous injections, in conjunction with an adjuvant such as Freund's complete or incomplete adjuvant. Following several booster immunizations, samples of serum are collected and tested for reactivity to Sak protein. Particularly preferred polyclonal antisera will give a signal on one of these assays that is at least three times greater than background. Once the titer of the animal has reached a plateau in terms of its reactivity to Sak protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Briefly, within one embodiment a subject animal such as a rat or mouse is injected with Sak protein. The Sak protein may be admixed with an adjuvant such as Freund's complete or incomplete adjuvant in order to increase the resultant immune response. Between one and three weeks after the initial immunization the animal may be reimmunized with another booster immunization, and tested for reactivity to Sak protein using assays described above. Once the animal has plateaued in its reactivity to Sak protein, it is sacrificed, and organs which contain large numbers of B cells such as the spleen and lymph nodes are harvested.

Cells which are obtained from the immunized animal may be immortalized by transfection with a virus such as the Epstein bar virus (EBV) (see Glasky and Reading, Hybridoma 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63 -Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, ie., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against Sak protein. A wide variety of assays may be utilized to determine the presence of antibodies which are reactive against Sak protein, including for example Countercurrent Immuno-Electrophoresis, Radioimmunoassays, Radioimmunoprecipitations, Enzyme-Linked Immuno-Sorbent Assays (ELISA), Dot Blot assays, Inhibition or Competition Assays, and sandwich assays (see U.S. Pat. Nos. 4,376,110 and 4,186,530; see also Antibodies: A Laboratory Manual, Harlow and Lane (eds.), Cold Spring Harbor Laboratory Press, 1988). Following several clonal dilutions and reassays, a hybridoma producing antibodies reactive against Sak protein may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al. supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Primers for mouse and human variable regions including, among others, primers for $V_{Ha}$, $V_{Hb}$, $V_{Hc}$, $V_{Hd}$, $C_{H1}$, $V_L$ and $C_L$ regions are available from Stratacyte (La Jolla, Calif.). These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

The polyclonal or monoclonal antibodies may be used to detect the kinase protein of the invention, or isoforms or parts thereof, in various biological materials, for example they may be used in an Elisa, radioimmunoassay or histochemical tests. Thus, the antibodies may be used to quantify the amount of a kinase protein of the invention, or an isoform or part thereof, in a sample in order to determine its role in particular cellular events or pathological states and to diagnose and treat such pathological states.

In particular, the polyclonal and monoclonal antibodies of the invention may be used in immuno-histochemical analyses, for example, at the cellular and sub-subcellular level, to detect the novel kinase protein of the invention, to localise it to particular cells and tissues and to specific subcellular locations, and to quantitate the level of expression.

Cytochemical techniques known in the art for localizing antigens using light and electron microscopy may be used to detect the novel kinase protein of the invention. Generally, an antibody of the invention may be labelled with a detectable substance and the novel kinase protein of the invention may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium. Antibodies may also be coupled to electron dense substances, such as ferritin or colloidal gold, which are readily visualised by electron microscopy.

Radioactive labelled materials may be prepared by radiolabeling with $^{125}I$ by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p., 215, Elsevier/North-Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

Indirect methods may also be employed in which the primary antigen-antibody reaction is amplified by the introduction of a second antibody, having specificity for the antibody reactive against the novel kinase protein of the invention. By way of example, if the antibody having specificity against the novel kinase protein of the invention is a rabbit IgG antibody, the second antibody may be goat anti-rabbit gamma-globulin labelled with a detectable substance as described herein.

Where a radioactive label is used as a detectable substance, the novel kinase protein of the invention may be localized by radioautography. The results of radioautography may be quantitated by determining the density of particles in the radioautographs by various optical methods, or by counting the grains.

As discussed above, the expression patterns found for the novel protein kinase of the invention indicate that it plays unique and important roles in cell proliferation. Therefore, the above described methods for detecting nucleic acid molecules and fragments thereof and Sak protein and parts thereof, can be used to monitor cell proliferation by detecting and localizing the novel kinase protein of the invention in organisms, tissues, and embryos.

It would also be apparent to one skilled in the art that the above described methods may be used to study the developmental expression of sak and, accordingly, will provide further insight into the role of Sak protein in cell proliferation.

The finding of a novel serine/threonine kinase protein which is expressed in proliferating cells permits the identification of substances which affect cell proliferation. A substance which affects expression of Sak protein and thus cell proliferation may be assayed using the above described methods for detecting nucleic acid molecules and fragments thereof and Sak protein or isoforms or parts thereof, by comparing the pattern and level of expression of the Sak protein or isoforms or parts thereof, in the presence and absence of the substance.

The invention also provides methods for identifying substances which are capable of binding to the Sak protein, or isoforms or parts thereof. Substances which can bind with the kinase protein of the invention or isoforms or parts thereof, may be identified by reacting the novel kinase protein of the invention or isoform or part of the protein, with a substance which potentially binds to the novel kinase protein, or isoform or part of the protein such as the kinase domain, and assaying for substance-protein complexes, for free substance or for non-complexed kinase protein, or isoform, or part of the protein, or for activation of the kinase protein.

Conditions which permit the formation of substance-protein complexes may be selected having regard to factors such as the nature and amounts of the substance and the kinase protein.

The substance-protein complex, free substance or non-complexed proteins or isoforms or parts thereof, may be isolated by conventional isolation techniques, for example, salting out, chromatography, electrophoresis, gel filtration, fractionation, absorption, polyacrylamide gel electrophoresis, agglutination, or combinations thereof.

To facilitate the assay of the components, antibody against the kinase protein or the substance, or a labelled kinase protein, or a labelled substance may be utilized. Antibodies, kinase protein or substance may be labelled with a detectable substance as described above.

The kinase protein or isoforms or parts thereof, or substance used in the method of the invention may be insolubilized. For example, the kinase protein or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized kinase protein or substance may be prepared by reacting the material with a suitable insoluble carrier using known chemical or physical methods, for example, cyanogen bromide coupling.

The above mentioned methods of the invention may be used to identify positive and/or negative regulators which bind with and catalytically activate the novel kinase protein of the invention thereby affecting cell proliferation. Identification and isolation of such Sak protein regulators will permit studies of the role of the regulators in the regulation of cell proliferation and permit the development of substances which affect this role, such as functional or non-functional analogues of the regulators. It will be appreciated that such substances will be useful as pharmaceuticals to modulate cell proliferation. Regulators which bind to and catalytically activate the novel kinase protein of the invention may be identified by assaying for protein serine/threonine kinase activity. Serine/threonine kinase protein activity may be assayed using known techniques such as those using anti-phosphoserine/phosphothreonine antibodies and labelled phosphorous. For example, immunoblots of a substance containing serine/threonine which is treated with a cataytically active kinase protein of the invention, or isoform or part thereof may be analyzed by autoradiography ($^{32}$P-labelled samples) or may be blocked and probed with antiphosphoserine or phosphothreonine antibodies.

The invention further contemplates a method for identifying a substance which is a substrate of an activated kinase protein of the invention or an isoform or part of the activated protein, comprising reacting an activated kinase protein of the invention, or isoform or part of the protein, with at least one substance which potentially is a substrate of the kinase protein, or isoform or part of the protein, under conditions which permit the phosporylation of the substance, and assaying for phosphorylation of the substance.

An activated kinase protein of the invention, or isoform or part thereof may be prepared by binding of a positive and/or negative regulator to the kinase protein of the invention, isoform or part thereof which results in activation of the catalytic domain.

Conditions which permit the phosphorylation of the substance may be selected having regard to factors such as the nature and amounts of the substance and the kinase protein. Phosphorylation of the substance may be determined using for example, labelled phosphorous as described above.

The invention also contemplates a method for assaying for an agonist or antagonist of the binding of the novel kinase protein of the invention, an isoform or part thereof, with a substance which is capable of binding with the novel kinase protein, preferably a positive and/or negative regulator or a substance which is a substrate. The agonist or antagonist may be an endogenous physiological substance or it may be a natural or synthetic drug.

In accordance with a preferred embodiment, a method is provided which comprises providing a known concentration of the novel kinase protein of the invention or an isoform or part thereof, incubating the protein, or isoform or part thereof, with a positive and/or negative regulator which can bind to and catalytically activate the protein or isoform or part thereof, and optionally a substance which is a substrate, and a suspected agonist or antagonist and assaying for activation of the kinase protein, or isoform or part thereof. Methods for assaying for activation of the kinase protein are described herein.

It will be understood that the agonists and antagonists that can be assayed using the methods of the invention may act on one or more of the binding sites on the kinase protein or regulator, including agonist binding sites, competitive antagonist binding sites, non-competitive antagonist binding sites or allosteric sites.

The invention also makes it possible to screen for antagonists that inhibit the effects of an agonist of the interaction of Sak protein with a Sak protein regulator or a substrate of the Sak protein. Thus, the invention may be used to assay for a substance that competes for the same regulator or substrate binding site on the novel kinase protein of the invention.

The invention further provides a method for assaying for a substance that affects cell proliferation comprising administering to a non-human animal or to a tissue of an animal, a substance suspected of affecting cell proliferation, and detecting, and optionally quantitating, the novel kinase protein of the invention in the non-human animal or tissue.

In another embodiment, the method may be used to assay for a substance that affects cell proliferation, comprising administering a substance suspected of affecting cell proliferation to a non-human animal having a proliferative disorder and detecting, and optionally quantitating, the novel protein kinase of the invention in the non-human animal. Examples of non-human animals having proliferative disorders include transplantable tumor models such as the B16 melanoma cell model. The effect of a substance may be assayed by injecting B16 melanoma cells into mice along with anti-sense sak and the substance to determine if the substance effects the ability of the antisense molecule to suppress growth.

Substances which are capable of binding to the kinase protein of the invention or isoforms or parts thereof, particularly regulators, agonists and antagonists of the binding of regulators and substrates of Sak protein identified by the methods of the invention, antisense nucleic acid molecules of the invention, and antibodies of the invention may be used for stimulating or inhibiting cell proliferation. The regulators, agonists and antagonists, substrates etc. may accordingly be used to stimulate or inhibit cell proliferation associated with disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections; and autoimmune diseases including systemic lupus erythematosus, Wegener's granulomatosis, rheumatoid arthritis, sarcoidosis, polyarthritis, pemphigus, pemphigoid, erythema multiforme, Sjogren's syndrome, inflammatory bowel disease, multiple sclerosis, myasthenia gravis, keratitis, scleritis, Type I diabetes, insulin-dependent diabetes mellitus, Lupus Nephritis, allergic encephalomyelitis. Substances which stimulate cell proliferation identified using the methods of the invention may be useful in the treatment of conditions involving damaged cells including conditions in which degeneration of tissue occurs such as arthropathy, bone resorption, inflammatory disease, degenerative disorders of the central nervous system; and for promoting wound healing.

Sak transcripts were found in meiotic spermatocytes and oocytes suggesting that substances identified using the method of the invention, and the antibodies and anti-sense nucleic acid molecules described herein may be useful as contraceptives. The substances, antibodies and anti-sense nucleic acid molecules may also affect the fertility of mammalian sperm.

The invention also relates to a pharmaceutical composition comprising a substance identified using the methods described herein or antibodies described herein.

The pharmaceutical compositions of the invention contain the substance or antibodies, alone or together with other active substances. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients', and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids.

The utility of the substances, antibodies, antisense nucleic acid molecules, and compositions of the invention may be confirmed in animal experimental model systems. For example, therapeutic utility in proliferative disorders may be tested by examining the ability of a substance etc. to suppress the growth of a transplantable tumor such as B16 melanoma cells. The utility of a substance etc. in fibrotic conditions may be tested by examining the susceptibility of mice to the induction of pulmonary fibrosis by bleomucin sulfate (Baecher-Allan, Regional Immunology 5(3–4):207, 1993). The well-characterized pig model of radiation induced fibrosis described in Martin et al, Radiation Research 134(1)63, 1993, and the experimental glomerulonephritis model described in Border et al, Nature 360:361, 1992 may also be utilised. Other models which may be useful in confirming the utility of the substances, antibodies and nucleic acid molecules of the present invention include those for wound healing (e.g. the fetal tissue repair model described in Bleacher et al. Dermatologic Clinics 11(4):677, 1993), bone repair (e.g. bone induction in rats—Yasko, A W, et al., Orthop. Trans. 15:501, 1991; sheep femur—Gerhart T N et al, Trans. 37 Annual Meeting Orthop. Res. Soc. Anaheim Calif. Catherson, B, ed) 16(1), p. 172, 1991; and dog mandible—Toriumi D M et al, Archiv. Otolaryngol. Head Neck Surg. 117:1101–1112, 1991), and autoimmune diseases (e.g. MRL-1pr/ipr mice are a model for systemic lupus erythematosus, and NZBxNZWf1 mice which demonstrate clinical symptoms comparable to those found with human autoimmune diseases—Theofilopoulos and Dixon, Adv. Immunol. 37, 1985).

The invention also provides methods for studying the function of the Sak protein. Cells, tissues, and non-human animals lacking in Sak expression or partially lacking in Sak expression may be developed using recombinant molecules of the invention having specific deletion or insertion mutations in the sak gene. For example, the kinase domain or parts thereof may be deleted. A recombinant molecule may be used to inactivate or alter the endogenous gene by homologous recombination, and thereby create a Sak deficient cell, tissue or animal.

Sak alleles may be generated in cells, such as embryonic stem cells by deletion mutation. A recombinant sak gene molecule may also be engineered to contain an insertion mutation which inactivates Sak. For example, a recombinant molecule may be engineered with an Asp mutation in the nucleic acids encoding the amino acid stretch KLAD*FGLAR (*marks point of mutation) in the kinase domain (van den Heuvel and E. Harlow, 1993, Science, 262:2050–2054). Such recombinant molecules may then be introduced into a cell, such as an embryonic stem cell, by a technique such as transfection, electroporation, injection etc. Cells lacking an intact sak gene may then be identified, for example by Southern blotting, Northern Blotting or by assaying for expression of Sak protein using the methods described herein. Such cells may then be fused to embryonic stem cells to generate transgenic non-human animals deficient in Sak. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on Sak expression.

The following non-limiting examples are illustrative of the present invention:

EXAMPLES

The following materials and methods were utilized in the investigations outlined in the examples:

cDNA cloning and molecular analysis.

A cDNA library was prepared in pCDM8 using poly(A)+ RNA from D33W25, a murine lymphoid tumor cell line (Dennis, J. W. (1986) *Cancer Res.* 46, 4594–4600). CHOP cells, a subline of CHO cells which expresses polyoma large T (LT) antigen were transiently transfected with the cDNA library using a modified DEAE-dextran procedure (Heffernan, M. & Dennis, J. W. (1991) *Nucleic Acids Research* 19, 85–92). After 72 hours, transfected cells were placed in selection medium containing 50 μg/ml of the cytotoxic lectin wheat germ agglutinin (WGA), and 3 weeks later plasmid DNA was recovered from the WGA resistant clones by the Hirt procedure (Hirt, B. (1967) *J. Mol. Biol.* 26, 365–369). Radiolabelled probes were prepared by random priming using the T7 Quick Prime kit (Pharmacia), and the dideoxynucleotide DNA sequencing method was used according to the manufacturers instructions (United States Biochemical Corporation). cDNA sequences were compared to the GenBank and EMBL databases using the FASTA program and amino acid alignments were done using the MALIGNED program, both from the University of Wisconsin Genetics Computer Group.

In situ RNA analysis.

In situ RNA hybridization was carried out on 8–10 μm cryostat sections, as described in Peter, M., Nakagawa, J., Doree, M., Labbe, J. C. & Nigg, E. A. (1990) *Cell* 60, 791–801. Adjacent sections were probed with antisense sak-a and sak-b. Control probes including a sak-a sense probe, the neuron-specific marker SCG10, as well as c-kit and Steel; the latter three probes gave specific non-overlapping patterns (data not shown). The 1.5 kb 17S fragment, unique to the sak-a transcript, was subcloned into PBSK (Stratagene) and antisense probes were generated by T7 RNA polymerase (probe 1, FIG. 1). To generate a sak-b specific probe the 3' end EcoRI/XhoI fragment (1.5 kb) was labelled with T3 RNA polymerase (probe 3, FIG. 1). Post-hybridization washings included treatment with 50 μg/ml RNase A at 37° C. or 42° C. for 30 minutes, and 2 stringent washes of 20 minutes each at 60° C. in 0.1X SSC. The slides were dipped in Kodak NTB-2 emulsion, exposed for 4–6 days, developed and stained with toluidine blue.

Sense and anti-sense sak expression vectors.

The hygromycin resistance gene driven by the β-actin promoter was excised from the pSP-β-hygroA vector (gift from Cecilia Moens and Dr. J. Rossant, Mount Sinai Hospital) by an EcoRV/PvuII digest and cloned into the ScaI site of pCDM8 vectors containing either no insert (control) or sense and antisense sak cDNA fragments under the control of the CMV promoter. For the colony formation assay, 30 μg of each plasmid was linearized by ClaI, HindIII or SacI and electroporated into 5×10⁶ CHO cells. Colonies were selected in α-MEM with 10% FCS and 400 μg/ml hygromycin B for 10 days. Colonies were stained in 0.06% methylene blue and 1.25% glutaraldehyde in PBS for 1 hour and then counted.

Example 1
Isolation of murine sak cDNAs.

In an attempt to clone genes regulating sialylation, a murine lymphoid cDNA library was transfected into CHOP cells, followed three days later by the addition of the sialic acid-binding lectin, WGA. From this screen, four WGA resistant CHOP clones retained episomal plasmid carrying an identical 1.5 kb cDNA insert (17S clone, FIG. 1), corresponding to a partial fragment of the sak-a gene (see below) in an antisense orientation. However, the relationship between the undersialylated phenotype and sak expression remains to be determined since transient transfections of CHOP cells with an expression vector containing this antisense fragment did not result in a high frequency of WGA-resistant colonies (data not shown).

Additional cDNA clones were isolated from the lymphoid cDNA library using the 17S partial cDNA fragment as a probe (probe 1, FIG. 1), and subsequently full-length clones were obtained by screening the library with a more 5' fragment (probe 2, FIG. 1). Sequence analysis of the isolated clones identified two transcriptional units, designated sak-a and sak-b (FIG. 1). The sak-a and sak-b cDNA likely represent alternatively spliced forms of the gene given that the sequences diverge after an AG dinucleotide (nt 1456, 1457), a sequence frequently found 5' to splice-donor sites (Padgett, R. A., Grabowski, P. J., Konarska, M. M., Seiler, S. & Sharp, P. A. (1986) *Ann. Rev. Biochem.* 55, 1119–1150). A 205 nt 5' untranslated region precedes the predicted start site of translation, with the AACATGG sequence surrounding the intitation site matching closely to the Kozak consensus for intiator methionines (Kozak, M. (1986) *Cell* 44, 283–292). The sak-a transcriptional unit encodes a 925 amino acid protein ($M_r$=103 kDa) and the sak-b encoded protein is 464 amino acids in length ($M_r$=53 kDa), with the first 416 amino acids of both proteins being identical but each having different C-terminal tails of 509 (FIG. 2, SEQ ID NOS:3 and 4) and 48 amino acids (FIG. 3, SEQ ID NOS:5 and 6), respectively. The 205 nt 5' untranslated region of sak is 71% G+C, and computer folding of this region suggests several energetically favourable secondary structures are possible (ie. delta G=–89 Kcal), which may reduce translational efficiency (14). In sak-a clones, 3' untranslated regions of 52 nt or 464 nt were identified, each containing a consensus polyadenylation signal (AATAAA) 22 nt and 20 nt upstream of a poly(A) tract, respectively (FIG. 2, SEQ. ID. NO.3). This region is A+T rich and contains three ATTTA sequences, features which have been shown to decrease the intracellular half-lives of transcripts (Shaw, G. & Kamen, R. (1986) *Cell* 46, 659–667). The sequence of the 3' untranslated region of the sak-b transcriptional unit is approximately 2 kb in length and lacks a poly(A) consensus signal and tail, suggesting the corresponding cDNA clones may not represent a full-length transcript (sequence not shown).

The N-terminal region common to both sak-a and sak-b proteins has significant homology to the polo subfamily of serine/threonine kinases, including the *Drosophila polo* kinase (Llamazares, S., Moreira, A., Tavares, A., Girdham, C., Spruce, B. A., Gonzales, C., Karess, R. E., Glover, D. M. & Sunkel, C. E. (1991) *Genes & Dev.* 5, 2153–2165), the murine snk protein (Simmons, D. L., Neel, B. G., Stevens, R., Evett, G. & Erikson, R. L. (1992) *Mol. and Cell. Biol.* 12, 4164–4169), the CDC5 kinase of *S. cerevisiae* (Kitada, K., Johnson, A. L., Johnston, L. H. & Sugino, A. (1993) *Mol. and Cell. Biol.* 13, 4445–4457) and the murine plk protein (Clay, F. J., McEwen, S. J., Bertoncello, I., Wilks, A. F. & Dunn, A. R. (1993) *Proc. Natl. Acad. Sci.* USA 90, 4882–4886) (ie. 42%, 41%, 39% and 37% identity, respectively). In addition, these proteins have a common structural organization with the kinase domain located in the N-terminus, followed by a C-terminal domain of unknown function. Given that sak is most closely related to the polo subfamily of kinases, and is the third murine member of this group, it has been named sak for snk/plk akin kinase.

An alignment of the kinase domains of sak and the polo subfamily members is shown in FIG. 4. The original four polo subfamily members contain the sequence GXGGFAXC within subdomain I, with both the alanine and cysteine residues being uncommon in these positions. The sak kinase contains the alanine residue of this motif, but the cysteine is replaced with valine, a residue more frequently found at this position in other serine/threonine kinases. The sak kinase domain also diverges significantly from other members of the polo subfamily in subdomain VI-B. Within this subdomain, the threonine residue in the sak sequence DLTLSN is in a position normally occupied by a lysine, not only in proteins within the polo subfamily, but in the majority of serine/threonine kinases. The serine residue in this sequence is replaced by a glycine in all other members of the polo subfamily. Sak also has the sequence GTPNY-ISPE in subdomain VIII which matches closely with the GTXXYXAPE consensus sequence characteristic of serine/threonine kinases (Hanks, S. K. & Quinn, A. M. (1991) *Methods. Enzymol.* 200, 38–63).

The C-terminal domains of Sak-a and Sak-b showed no significant similarities to each other or to any sequences found in the databank. In addition, a 30 amino acid homology domain identified in the C-terminus of the polo, CDC5, plk and snk kinases is absent in both of the predicted sak proteins (Clay, F. J., McEven, S. J., Bertoncello, I., Wilks, A. F. & Dunn, A. R. (1993) *Proc. Natl. Acad. Sci.* USA 90, 4882–4886). Three PEST regions, each containing 2 sequences in tandem in Sak-a and one in Sak-b, were identified in the C-terminal region of the proteins (In FIG. 2, the PEST amino acid sequences are boxed with the middle basic residue breaking the sequence in two PEST regions). PEST sequences are rich in proline, serine, threonine, aspartate and glutamate residues, and flanked on either side by a basic amino acid. They are found in a number of proteins with short intracellular half-lives and appear to contribute directly to message instability (Rogers, S., Wells, R. & Rechsteiner, M. (1986) *Science* 234, 364–368).

Example 2
Tissue Specific Expression of sak.

Figure 5:
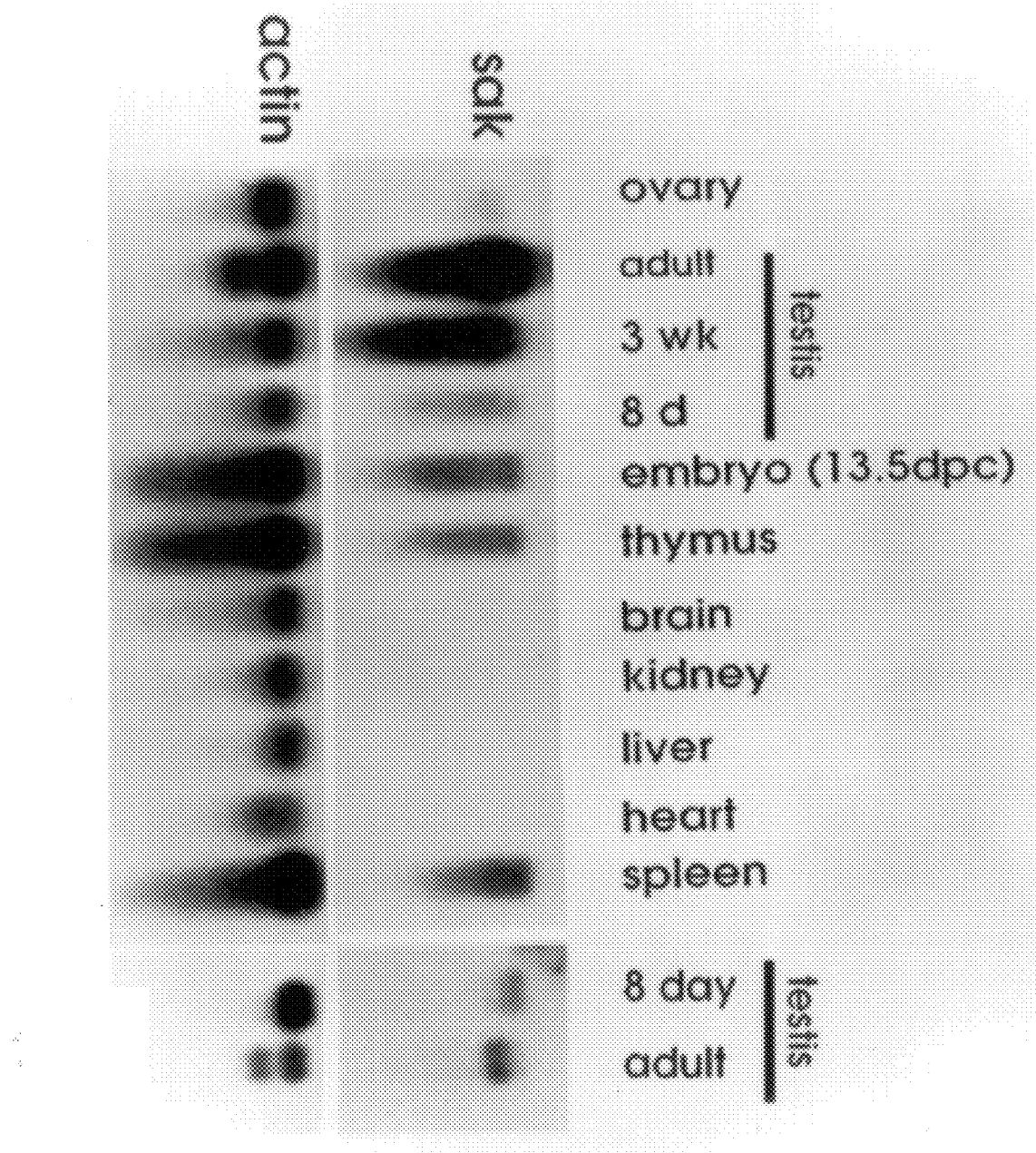
FIG. 5 is a gel showing Northern analysis of sak-a expression in murine tissues.

Total RNA (10 ug) from mouse tissues was separated by agarose gel electrophoresis, transferred to a nylon membrane and probed with either a sak-a (17S probe, FIG. 1) or a β-actin probe. The right-most two lanes of testis RNA from 8 day and adult mice more clearly demonstrates the change in sak-a transcript size (4.5 kb to 4.0 kb) that occurs following pubertal maturation. Northern analysis of adult tissues showed sak-a expression to be most abundant in the testis compared to all other tissues examined (FIG. 5). Transcript levels in the testis were comparatively low at day 8 (ie. pre-meiosis) and increased with age in a manner that reflects the increase in meiotic activity occurring at these time points. Interestingly, a 4.5 kb transcript was detected at day 8, while a 4 kb transcript was predominant in three week old and adult testis (FIG. 5). 4.5 and 4.0 kb transcripts were also detected at lower levels in the spleen, thymus, ovary and 12.5 dpc (days postconception) embryonic RNA and not in the heart, liver, kidney or brain. Northern blots probed with sequences unique to the 3' untranslated region of sak-b (probe 3, FIG. 1) identified transcripts of 3.5 kb and 4 kb that were expressed at several fold lower levels than sak-a but with the same tissue specific patterns, including the stage-specific change in expression level and transcript size seen in the testis upon maturation (data not shown).

Example 3
Spatial Localization of sak Transcripts by in situ Hybridization.

To analyse sak expression during embryonic development, $^{35}$S-labelled antisense probes specific to the sak-a (probe 1, FIG. 1) or sak-b (probe 3, FIG. 1) transcripts were hybridized in situ to sections of embryos at different gestational stages.

FIG. 6 shows the RNA in situ localization of sak-a expression during murine embryonic development. (A) Bright and (B) dark field photomicrographs of sagittal sections through 7.5 dpc embryo embedded in the uterus hybridized with a sak-a probe. (C) Bright and (D) dark field photomicrographs of sagittal sections through a 11.5 dpc embryo hybridized with a sak-a probe. (E,K,M) Bright and (F,L,N) dark field photomicrographs of sagittal sections through a 17.5 dpc embryo hybridized with a sak-a probe. Arrowheads in (K) mark the border between the olfactory and respiratory epithelia. (G) Bright field photomicrograph of a coronal section through a 13.5 dpc embryo with adjacent sections probed with (H) sak-a (I) SCG10 and (J) sense sak-a control. 4v, fourth ventricle; ac, amniotic cavity; aq, aqueduct; bl, basal layer; de, decidua; ec, ectoplacental cone; es, esophagus; ex, exocoelom; gu, gut; he, heart; Jo, Jacobsons organ; ki, kidney; la, larynx; li, liver; lu, lung; lv, lateral ventricle; mp, maxillary palate; nc, nasal cavity; np, nasopharynx; ns, nasal septum; ob, olfactory bulb; oe, olfactory epithelium; ol, olfactory pit; op. oropharynx; re, respiratory epithelium; sc, spinal cord; st, stomach; tb, turbinate bone; th, thymus; to, tongue; tr, trachea; ur, urogenital ridge.

FIG. 7 shows RNA in situ localization of sak expression in the adult gut and gonads. All sections were hybridized with a sak-a specific probe as described herein. (A). Bright and (B) dark field photomicrographs of sections through the ovary of a superovulated female induced by pregnant mare serum gonadotropins. gr, granulosa cell; oo, oocyte. (C) Bright and (D) dark field photomicrographs of sections through an adult testis. Le, Leydig cell; sg, spermatogonia; sp, spermatocyte; st, spermatids. (E) Bright and (F) dark field photomicrographs of sections through the adult gut. cr, crypt cells; il, intestinal lumen; sm, smooth muscle layer; vi, villi.

Figure 6A:
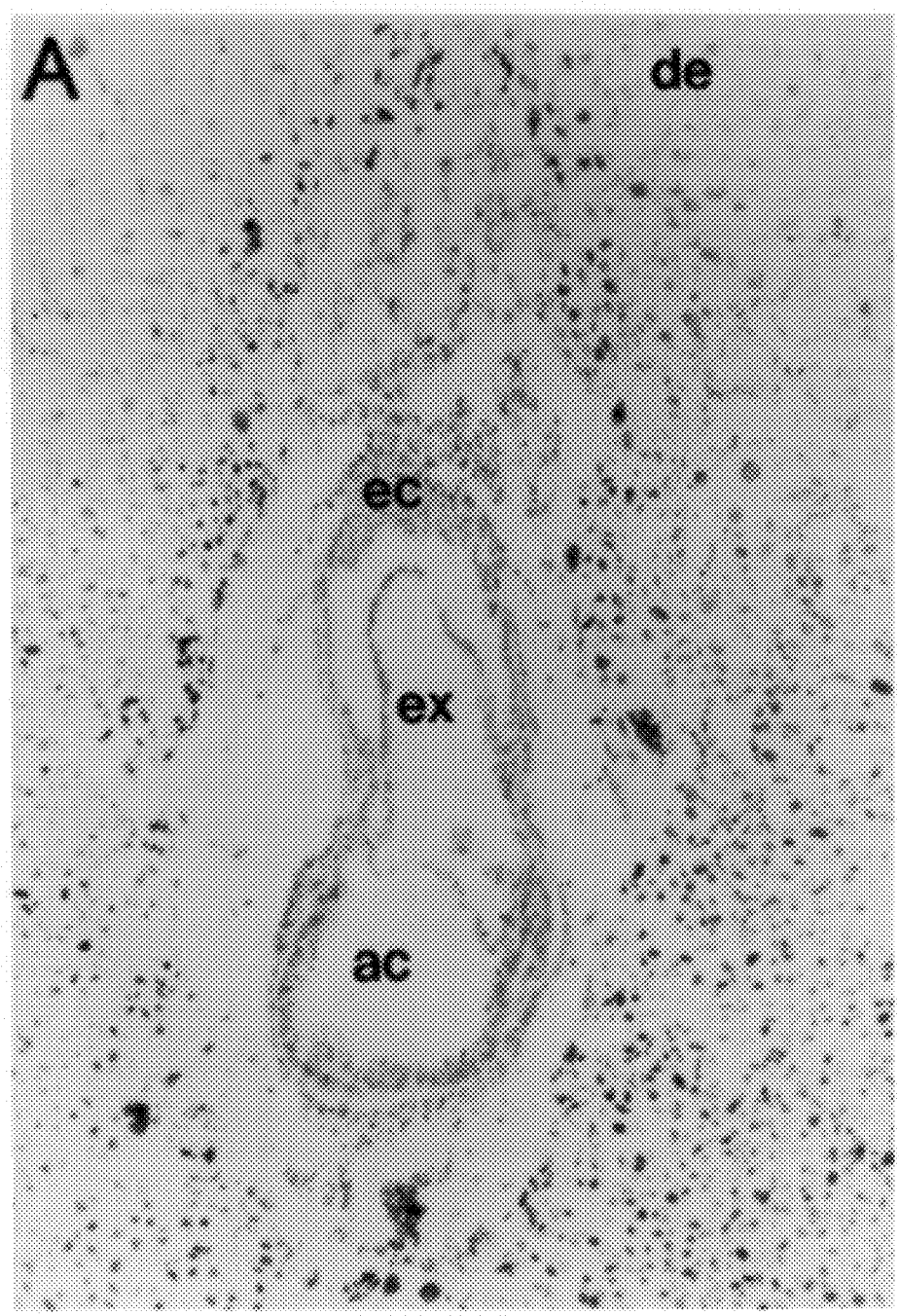
FIG. 6 shows (A) bright and (B) dark field photomicrographs of sagittal sections through 7.5 dpc embryo embedded in the uterus hybridized with a sak-a probe, (C) bright and (D) dark field photomicrographs of sagittal sections through a 11.5 dpc embryo hybridized with a sak-a probe; (E,K,M) bright and (F,L,N) dark field photomicrographs of sagittal sections through a 17.5 dpc embryo hybridized with a sak-a probe; (G) bright field photomicrograph of a coronal section through a 13.5 dpc embryo with adjacent sections probed with (H) sak-a (I) SCG10 and (J) sense sak-a control.
Figure 6B:
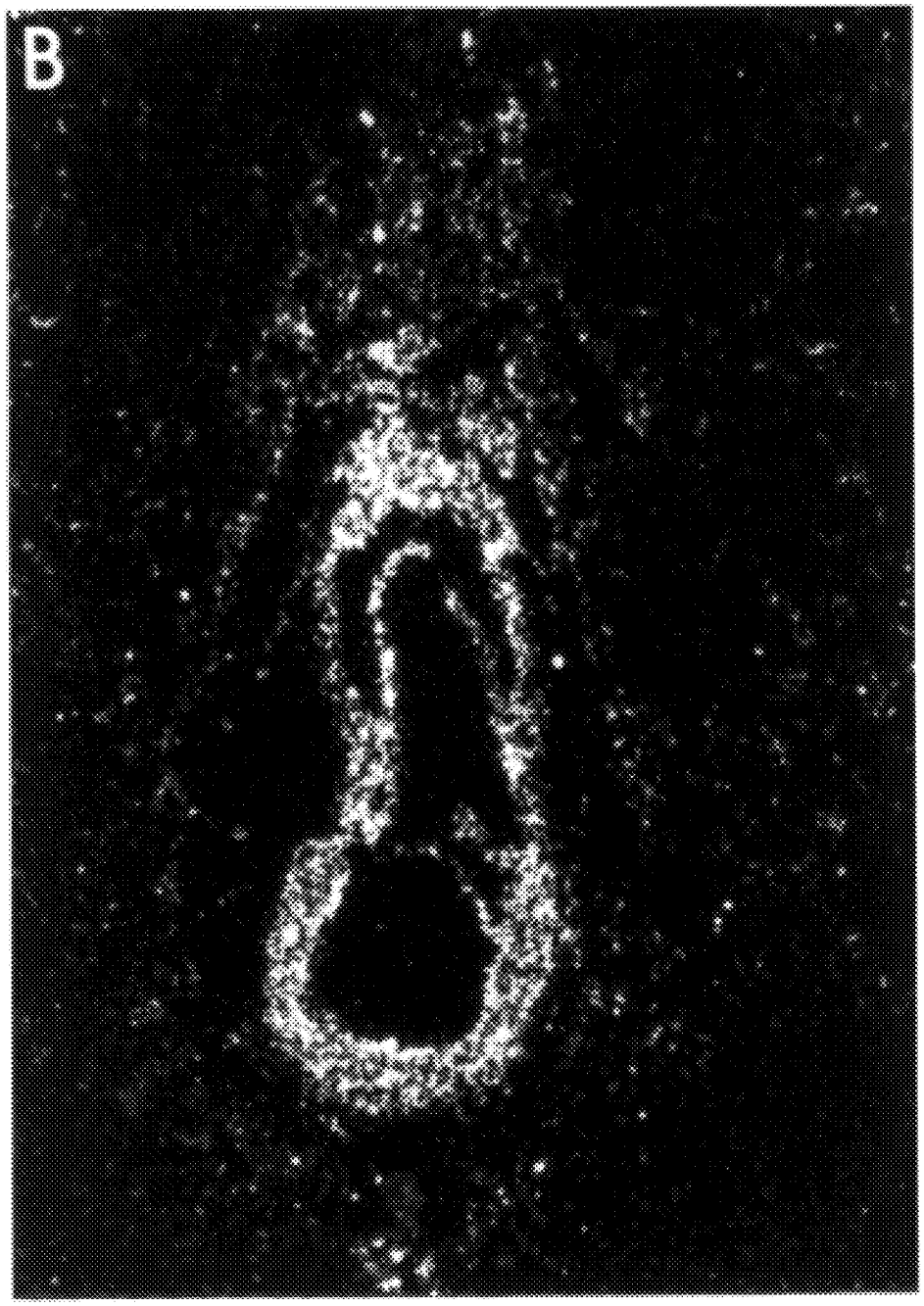
Figure 6C:
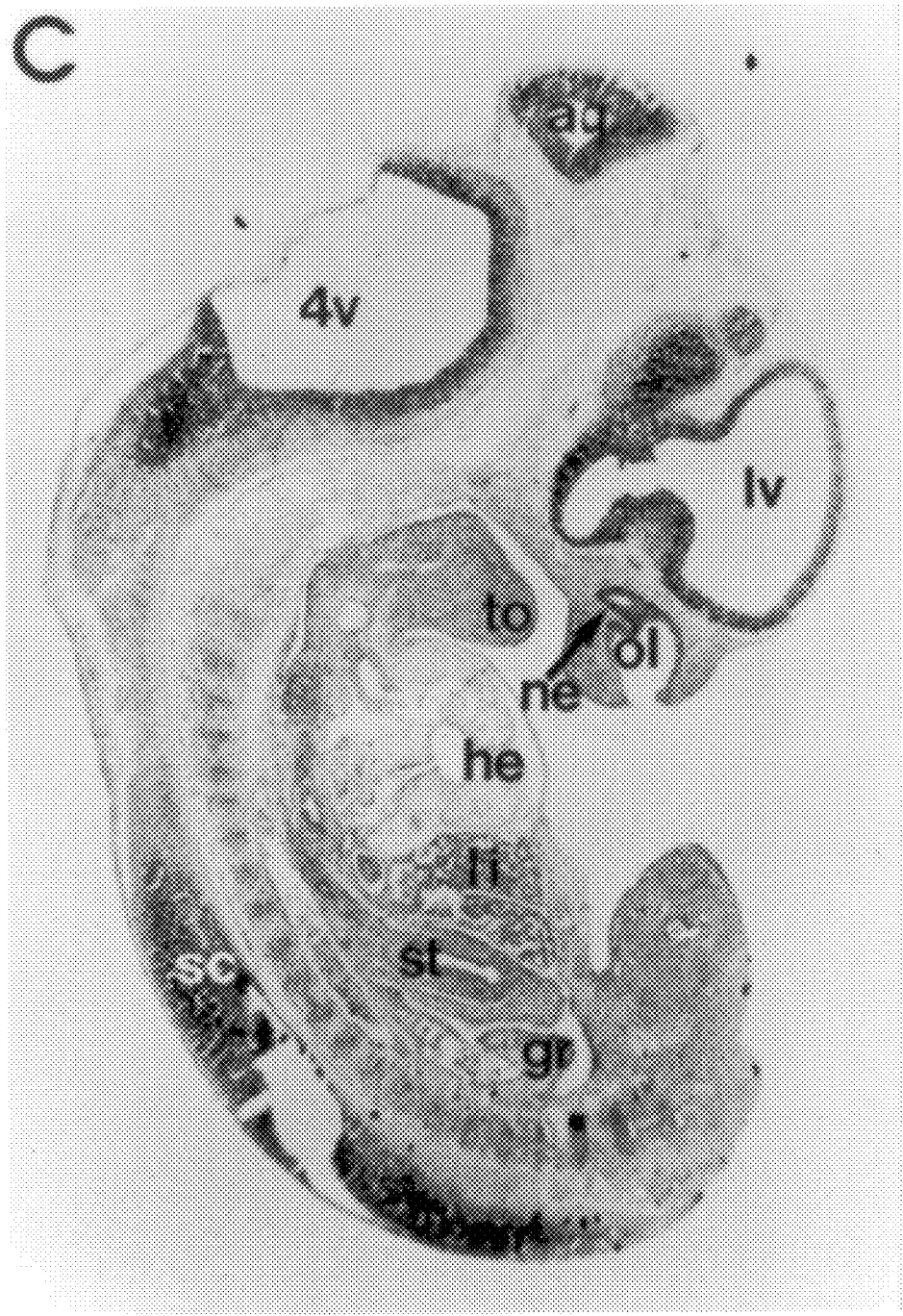
Figure 6D:
Figure 6E:
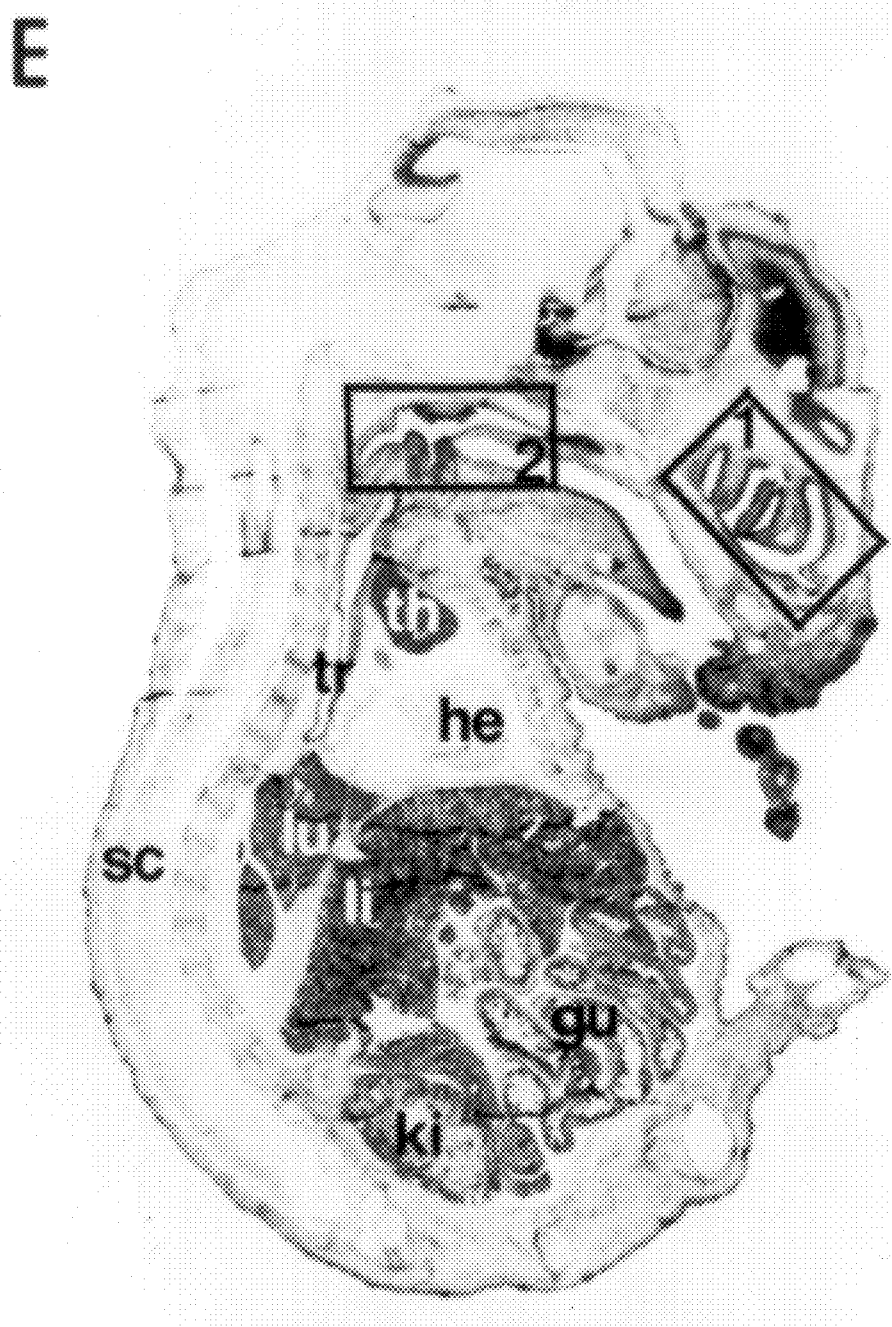
Figure 6F:
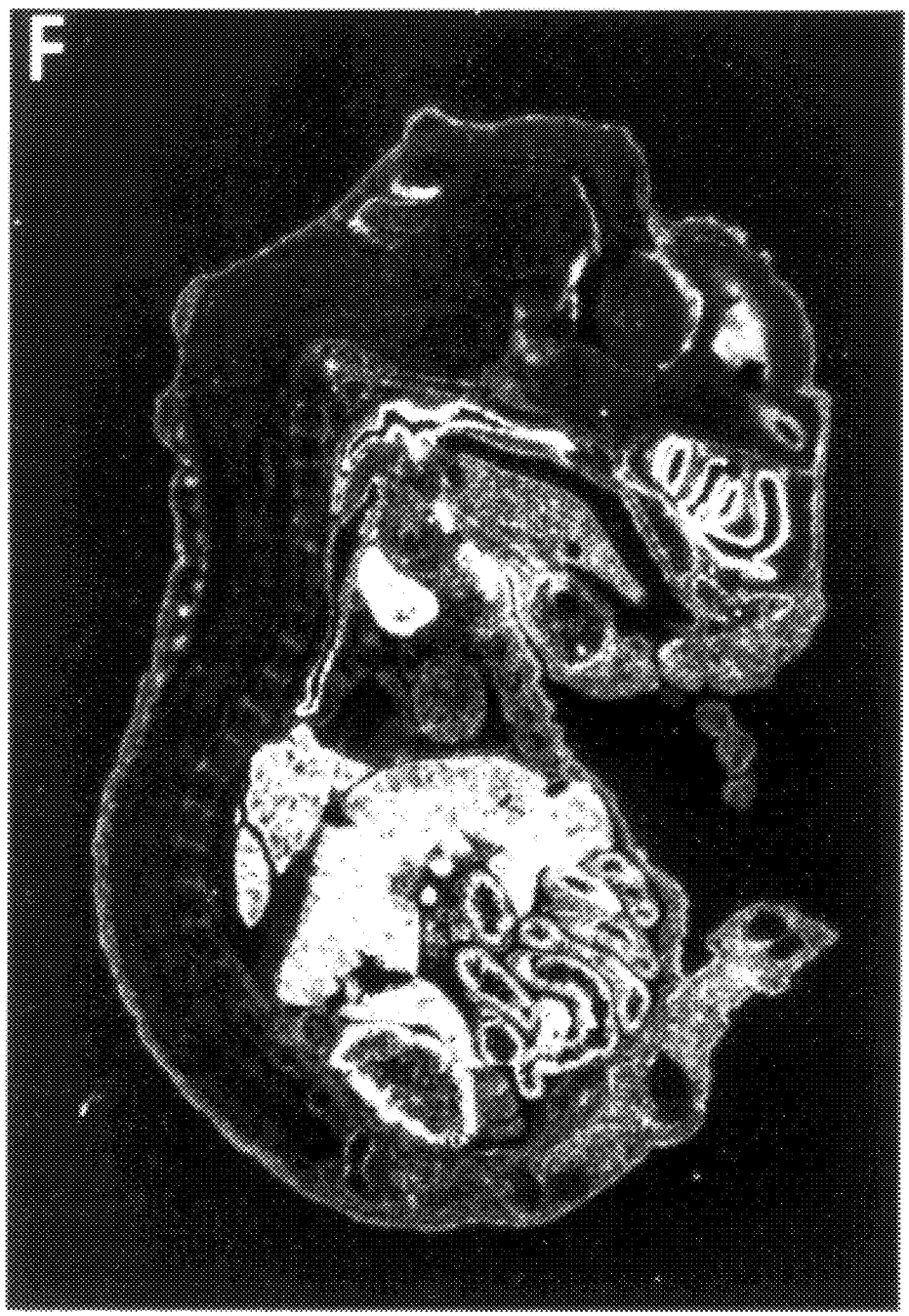
Figure 6G:
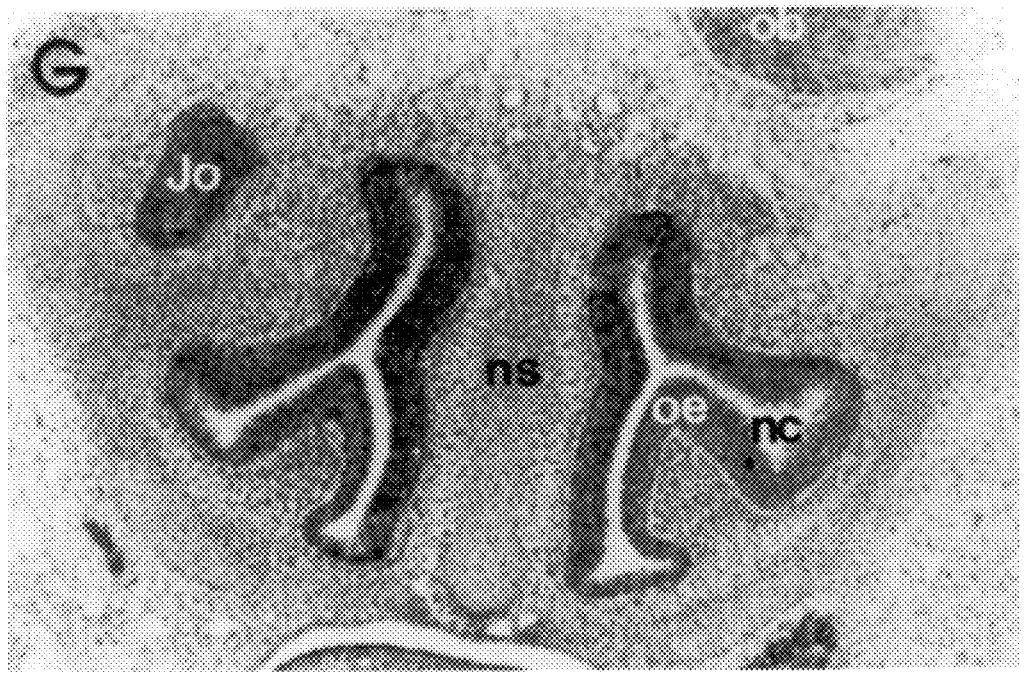
Figure 6H:

The expression patterns of sak-a and sak-b were similar but the relative amount of transcripts was much higher for sak-a. At the 7.5 dpc primitive streak stage, sak transcripts were evenly distributed in both embryonic and extraembryonic tissues and much lower levels were detected within the maternal decidua (FIG. 6B). With the onset of organogenesis, sak expression became more restricted in a manner that reflected the regionalization of proliferating zones. For example, sak expression in the central nervous system (CNS) was confined to the ventricular zones of the brain and spinal cord at all stages of development of these structures [eg. 11.5 dpc (FIG. 6D), 17.5 dpc (FIG. 6F)]. During embryogenesis, expression of sak was detected within many organs during their proliferative stages, including the skin, liver, thymus, small intestine, and the cortical layer of the kidney (FIG. 6D, 6F). In the adult small intestine, sak expression was restricted to the region at the base of the crypts where cell division is occurring and could not be detected in the epithelium lining the villi (FIG. 6F).

Figure 6I:
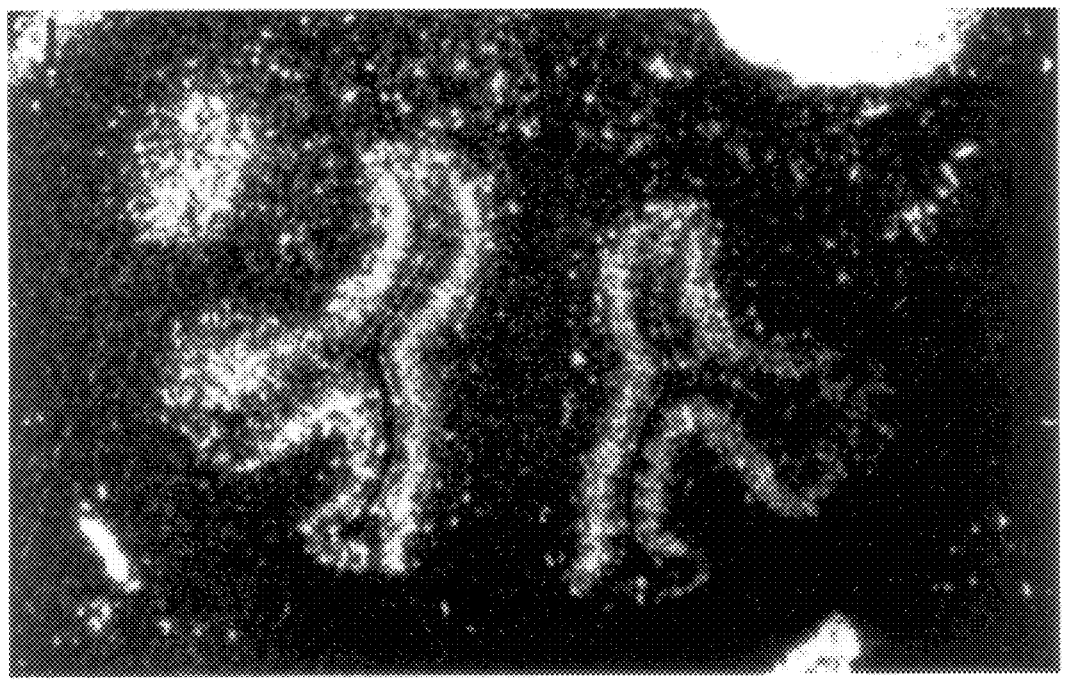

Interestingly, sak transcripts were particularly prominent during embryogenesis in the nasal cavity within both the olfactory and nasal mucosa (FIG. 6D, 6F). To examine expression in the olfactory epithelium more closely, consecutive sections cut through the head of a 13.5 dpc embryo were hybridized with sak (FIG. 6H) and SCG10 (FIG. 6I). In transverse sections through the head of 13.5 dpc embryos, sak hybridized to a region basal to the olfactory neuron layer identified by the neuron specific SCG10 probe (Stein, R., Mori, N., Matthews, K., Lo, L.-C. & Anderson, D. J. (1988)

Figure 6J:
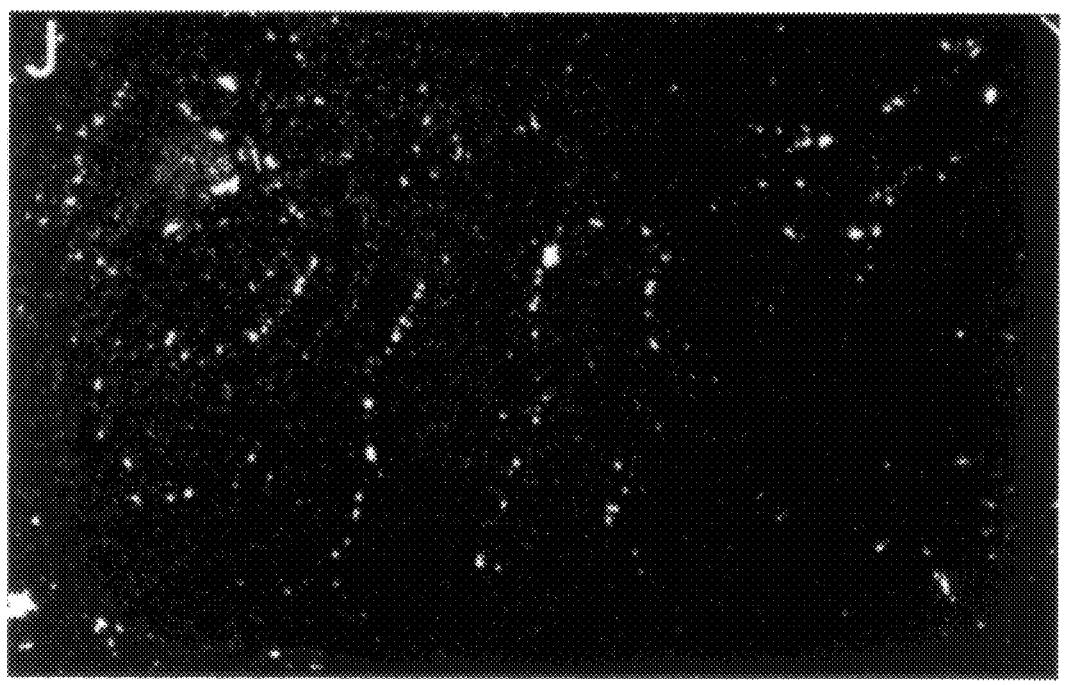
Figure 6K:
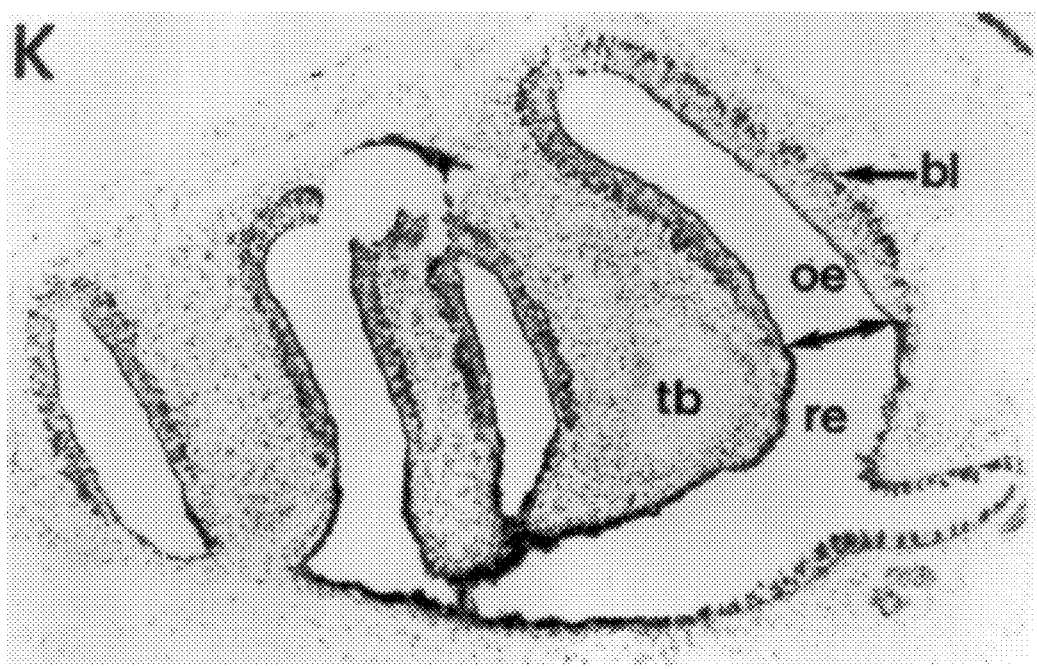
Figure 6L:
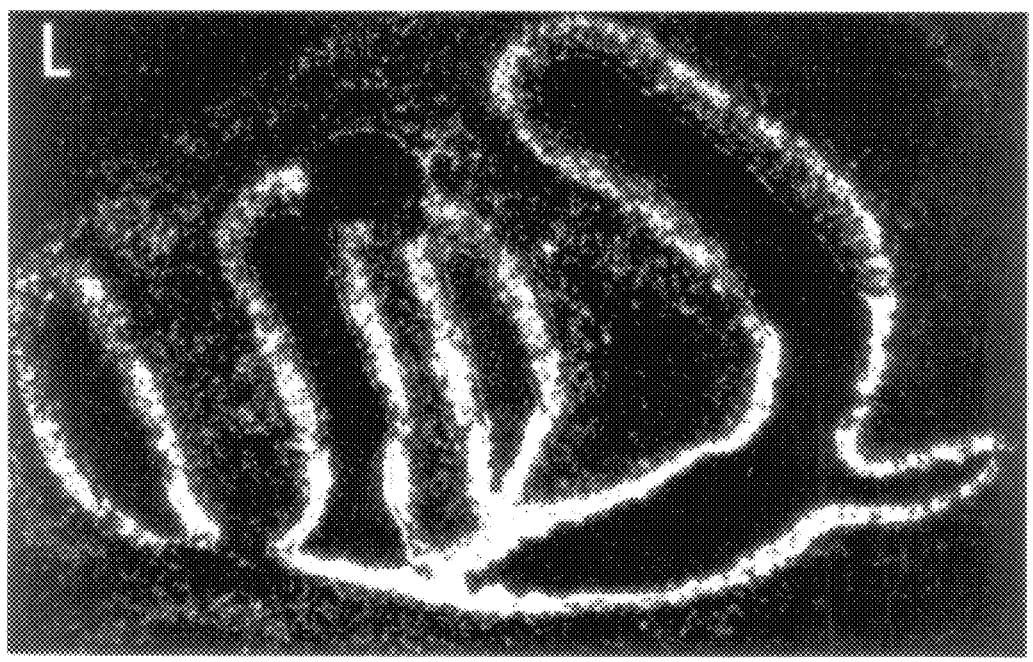
Figure 6M:
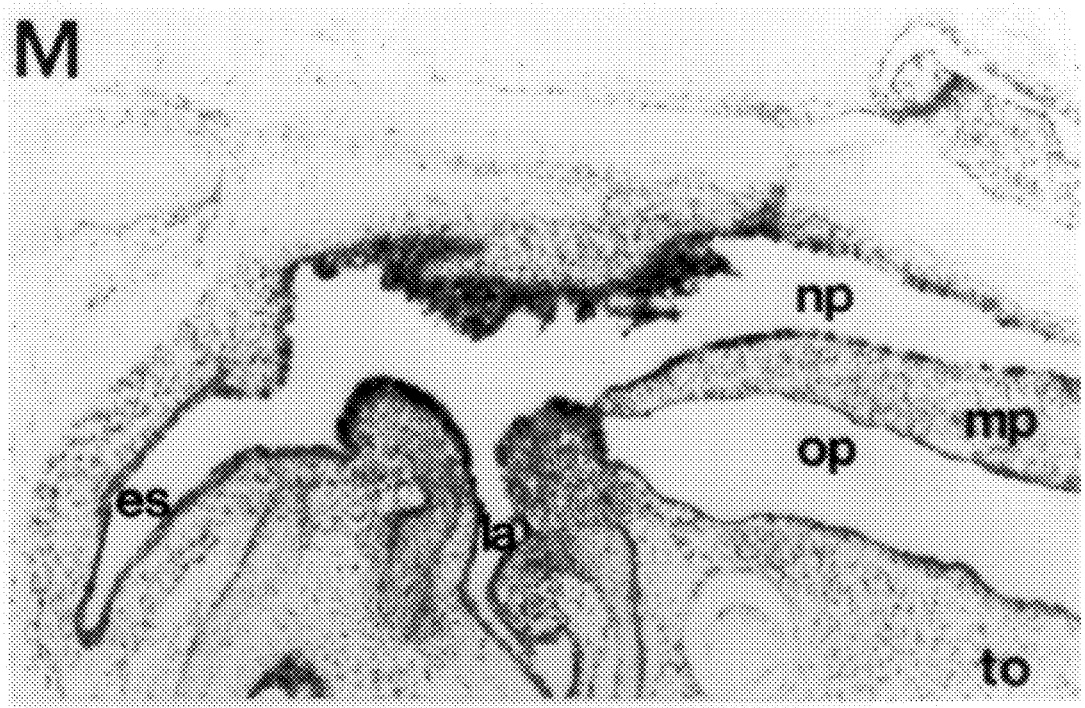
Figure 6N:

Neuron 1, 463–476), suggesting that sak is expressed in the basal layer of the olfactory epithelium and not in the epithelial or neuronal layers. In these sections, sak expression was also detected in the vomeronasal organ, which contains an accessory olfactory epithelium resembling the olfactory mucosa. Control sections hybridized with a sak sense probe did not show expression in these regions, confirming the specificity of this expression pattern (FIG. 6J). Expression in the basal cell layer of the olfactory epithelium persisted until at least day 17.5 pc (FIG. 6F, 6L). In addition, at day 17.5 pc high levels of sak transcripts were detected in the epithelium lining the nonneuronal portion of the nasal cavity (FIG. 6F, 6L) an expression pattern which continued into the similarly structured epithelial layer of the upper respiratory tract, bronchi and large bronchioles (FIG. 6F, 6N).

Figure 7A:
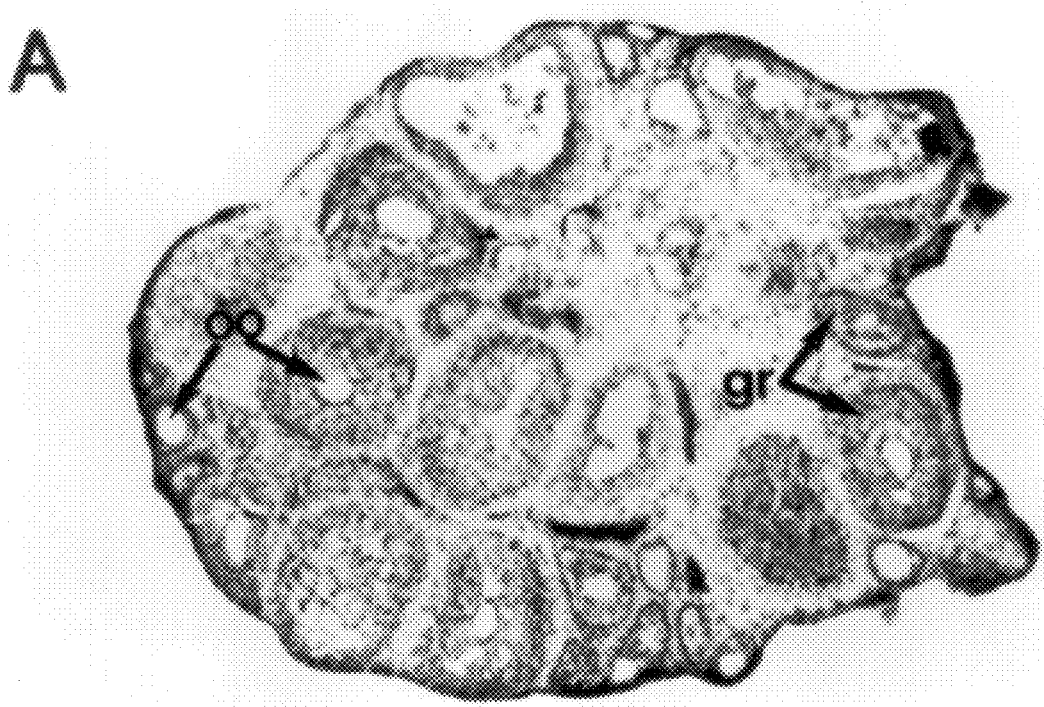
FIG. 7 shows (A) bright and (B) dark field photomicrographs of sections through the ovary of a superovulated female induced by pregnant mare serum gonadotropins; (C) bright and (D) dark field photomicrographs of sections through an adult testis; and (E) bright and (F) dark field photomicrographs of sections through the adult gut.
Figure 7B:
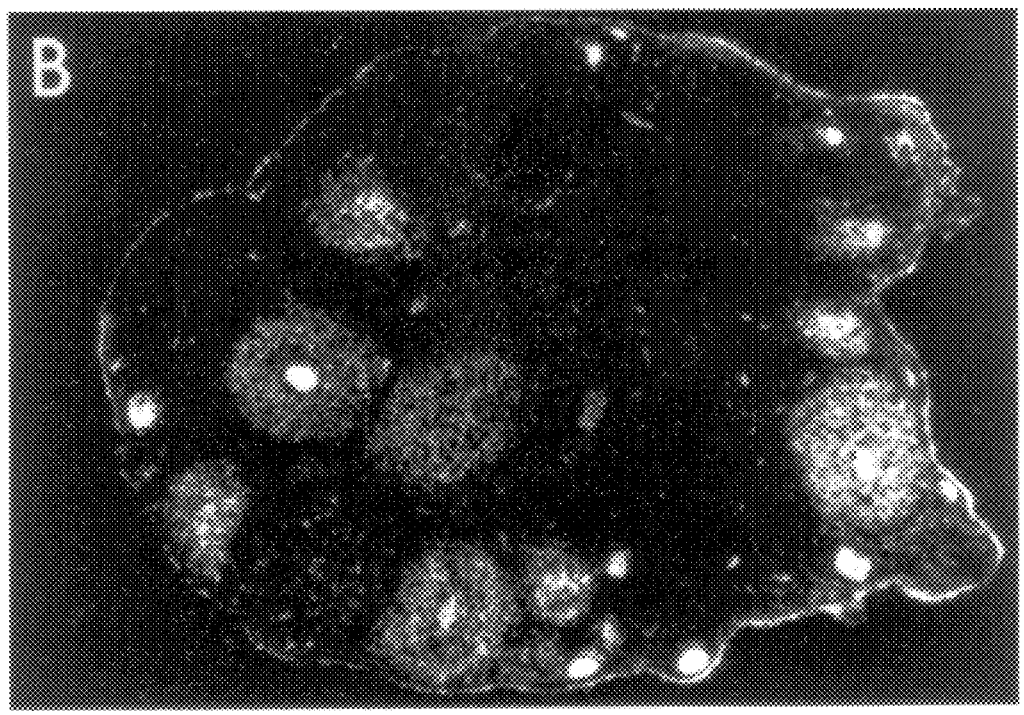
Figure 7C:
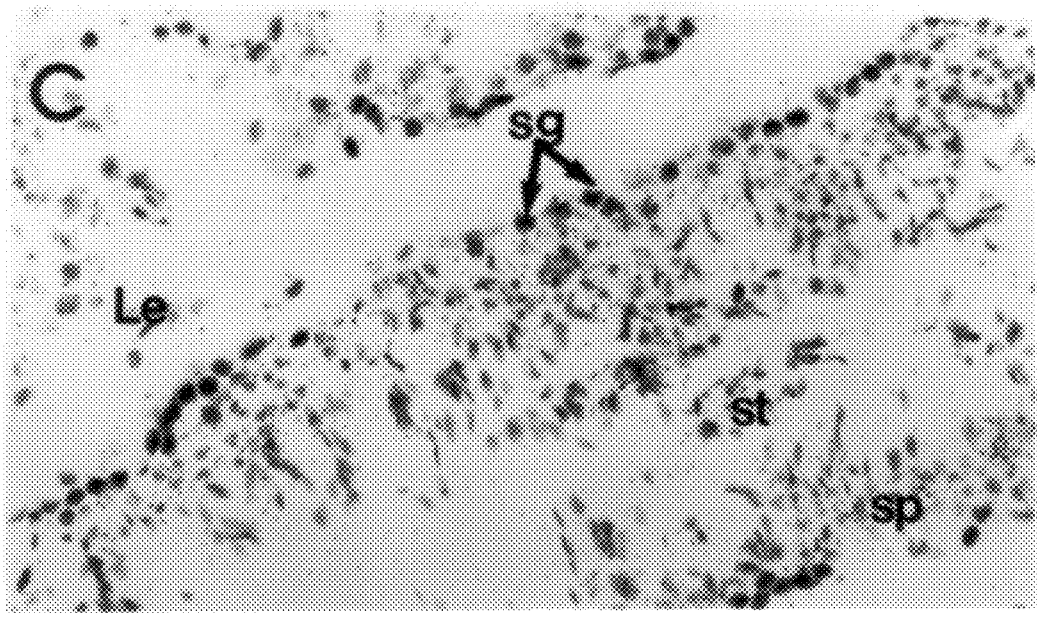
Figure 7D:
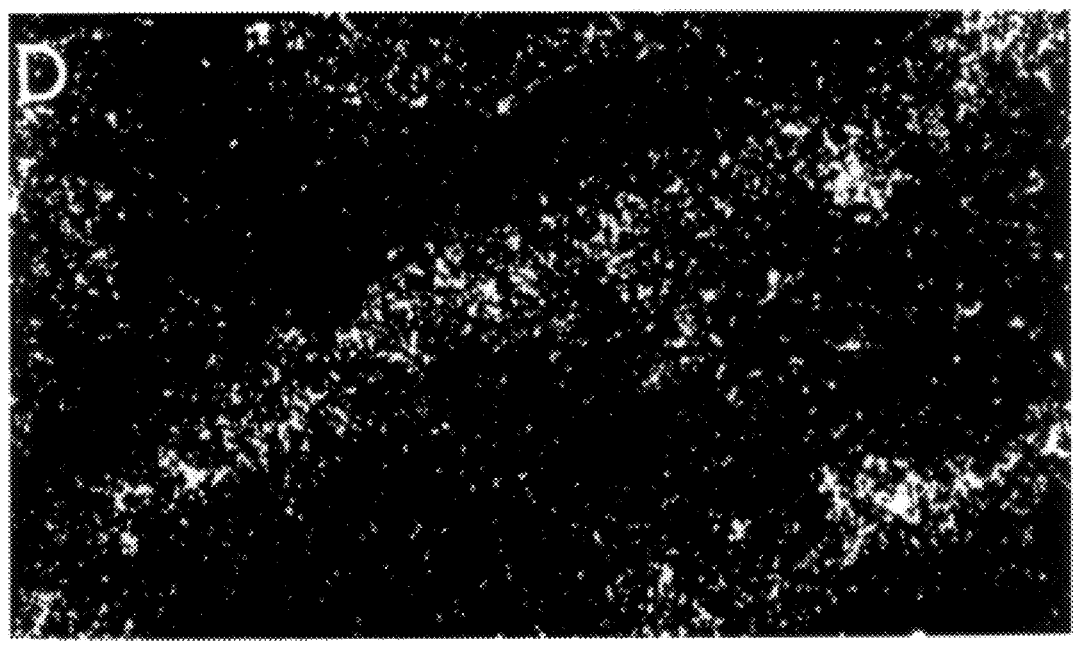
Figure 7E:
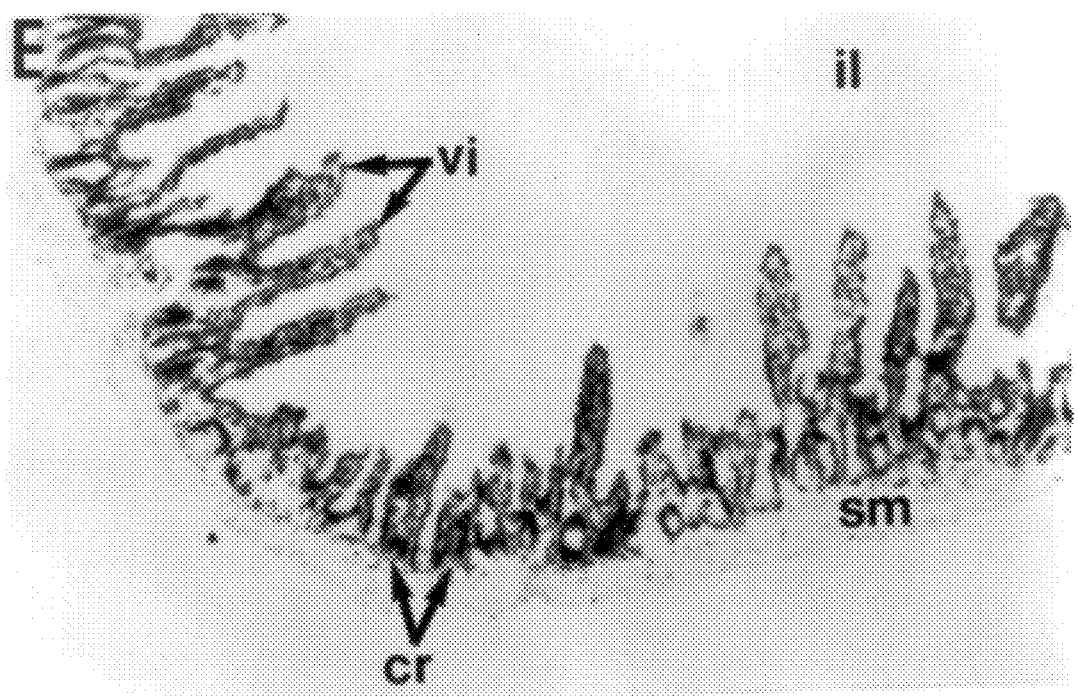
Figure 7F:
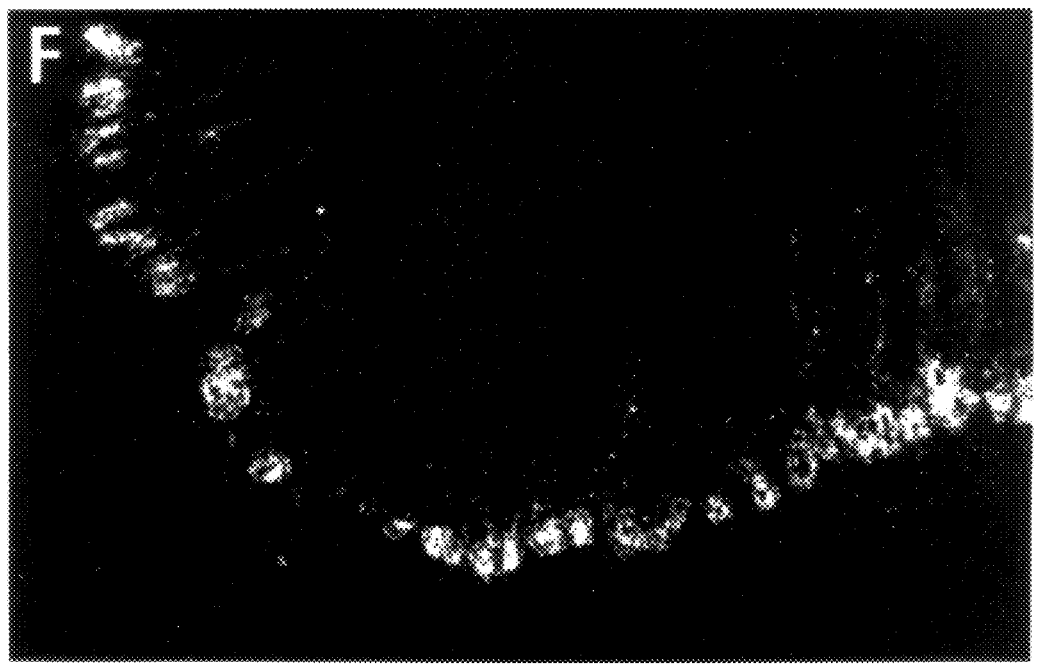

In sections through the testis the highest levels of expression were in the meiotically dividing spermatocytes and much lower levels were seen in the spermatogonia, the immediate post-meiotic round spermatids and mature spermatozoa (FIG. 7D). No expression was detected in the epithelial Sertoli cells or stromal Leydig cells. Examination of gonadotropin superovulated ovaries at different stages of the cycle revealed high levels of sak expression in oocytes during all phases of growth. Lower levels of sak transcripts were also detected within the granulosa cells after the initiation of follicular growth by pregnant mare serum gonadotropins, with expression levels correlating with the proliferative state.

Example 4
Expression of a sak-a Antisense Fragment Suppressed Cell Proliferation.

To determine whether sak expression is required for cell growth, an antisense approach was used to examine the effect of decreasing expression of this gene on the ability of CHO cells to form colonies. Colony formation has been used to assess the ability of cyclin D1 (Quelle, D. E., Ashmun, R. A., Shurtleff, S. A., Kato, J-y., Bar-Sagi, D., Roussel, M. F. & Sherr, C. J. (1993) *Genes & Dev.* 7, 1559–1571) as well as the p53 (Baker, S. J., Markowitz, S., Fearon, E. R., Willson, J. K. V. & Vogelstein, B. (1993) *Science* 249, 912–915) and retinoblastoma (Qin, X-q., Chittenden, T., Livingston, D. M. & Kaelin, W. G. Jr. (1992) *Genes & Dev.* 6, 953–964) tumor suppressor genes to suppress cell growth. Growth suppression was measured by transfecting CHO cells with a vector expressing both the antisense sak-a (17S) fragment and the hygromycin B resistance gene. In particular, CHO cells were transfected with pCDM8 vectors containing cDNA inserts under the control of the CMV promoter and the hygromycin resistance cassette. The ClaI digests linearized the vector, and the HindIII cut the vector between the CMV promoter and the antisense sak cDNA to prevent expression of this fragment. Transfected cells were selected in hygromycin B for 10 days and then enumerated. The results are expressed as a percentage of colony formation in cultures transfected with construct #1, which produced 318, 239, 159 colonies per $5 \times 10^5$ transfected cells in 3 independent experiments. Antisense sak-a expression decreased the efficiency of colony formation in the presence of hygromycin B by twenty-fold compared to cells transfected with vector containing only the hygromycin resistance gene, whereas expression of sense sak-a or sak-b had little or no effect on colony formation (Table 1). In addition, digesting the antisense construct between the CMV promoter and the 17S insert with HindIII (Table 1) or SacI (data not shown) restored colony formation to normal levels, demonstrating that antisense expression is responsible for the inhibition of cell growth.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications are herein incorporated by reference in their entirety to the same extent as if each individual publication, patent or patent application was specifically and individually indicated to be incorporated by reference in its entirety.

The following sequence listings form part of the application.

TABLE 1

Suppression of Colony Formation by Antisense sak-a

| Construct | Digestion | % hygromycin B-resistant colonies | n |
|---|---|---|---|
| No Sak insert | Cla I | 100 | 3 |
| Sak-a antisense | Cla I | 4.2 +/− 1.6 | 3 |
| Sak-a antisense | HindIII | 87 | 1 |
| Sak-a sense | Cla I | 85 | 1 |
| Sak-b sense | Cla I | 82 | 1 |

We claim:

1. A method for identifying a substance which binds a serine/threonine tyrosine kinase protein comprising the steps of:

(a) reacting a serine/threonine tyrosine kinase protein with a test substance under conditions which permit binding of the protein and test substance, wherein the protein has serine/theonine tyrosine kinase activity and comprises the amino acid sequence as shown in SEQ ID. NOS:2, 4, or 6, or a fragment of any of the amino acids shown in SEQ ID. NOS:2, 4, or 6; and (b) assaying for binding;

wherein the detection of binding indicates that the test substance binds to the protein.

2. A method for identifying a substance which binds a serine/threonine tyrosine kinase protein and acts as a positive or negative regulator of the protein comprising the steps of:

(a) reacting a serine/threonine tyrosine kinase protein with a test substance under conditions which permit binding of the protein and test substance, wherein the protein has serine/threonine tyrosine kinase activity and comprises the amino acid sequence as shown in SEQ ID. NOS:2, 4, or 6, or a fragment of any of the amino acids shown in SEQ ID. NOS:2, 4, or 6; and (b) assaying for binding and serine/threonine tyrosine kinase activity;

wherein the detection of binding and increased activity relative to activity in the absence of the test substance indicates that the test substance is a positive regulator, and the detection of binding and decreased activity relative to activity in the absence of the test substance indicates that the test substance is a negative regulator.

3. A method for identifying a substrate of a serine/threonine tyrosine kinase protein comprising the steps of:

(a) reacting a serine/threonine tyrosine kinase protein with a potential substrate under conditions which permit serine/threonine tyrosine kinase activity, wherein the protein has serine/threonine tyrosine kinase activity and comprises the amino acid sequence as shown in SEQ ID. NOS:2, 4, or 6, or a fragment of any of the amino acids shown in SEQ ID. NOS:2, 4, or 6; and (b) assaying for phosphorylation of the potential substrate;

wherein the detection of phosphorylation indicates that the potential substrate is a substrate of the protein.

4. A method for assaying for an agonist or antagonist of the interaction of a serine/threonine tyrosine kinase protein and a substance that binds to the protein comprising the steps of:

(a) reacting a serine/threonine tyrosine kinase protein with the substance, and a potential agonist or antagonist under conditions which permit the protein to bind to the substance, wherein the protein has serine/threonine tyrosine kinase activity and comprises the amino acid sequence as shown in SEQ ID. NOS:2, 4, or 6, or a fragment of any of the amino acids shown in SEQ ID NOS:2, 4, or 6; and (b) assaying for binding of the protein and the substance, or serine/threonine tyrosine kinase activity;

wherein the detection of increased binding or activity relative to binding or activity in the absence of the potential agonist or antagonist indicates an agonist, and the detection of decreased binding or activity relative to binding or activity in the absence of the potential agonist or antagonist indicates an antagonist.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1453 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
    (A) ORGANISM: Mus musculus
    (D) DEVELOPMENTAL STAGE: Lymphoid cDNA Library (vii) IMMEDIATE SOURCE:
    (A) LIBRARY: Murine Lymphoid
    (B) CLONE: WGA-Resistant Chop Clones (ix) FEATURE:
    (A) NAME/KEY: CDS
    (B) LOCATION: 206..1453

(ix) FEATURE:
    (A) NAME/KEY: 5'UTR
    (B) LOCATION: 1..205

(xi) SEQUENCE DESCRIPTION: SEQ ID NO:1:

```
GCGGGAATTT TTCAAAATGG GAGCTCCGGG GCGCCGCCCA GGCCTCGGGA GGTACCGGGG      60

GTACCTTTCG GTGGCGTTGG CGGCGTCGCC AGCGGCGGCG TAGAGAAGGC GTCCTGATGG     120

GCGCCAAGAC CTGCTGGCTT CTCGGAGCGC TGCCTCGGAG GGGACTGCGA AAGGCCGAG     180

CCCCGGGCGC CGGCGGCTCG GGAAC ATG GCG GCG TGC ATC GGG GAG AGG ATC      232
                             Met Ala Ala Cys Ile Gly Glu Arg Ile
                              1               5

GAG GAC TTT AAG GTT GGA AAT CTA CTC GGT AAA GGA TCA TTT GCT GGT      280
Glu Asp Phe Lys Val Gly Asn Leu Leu Gly Lys Gly Ser Phe Ala Gly
 10              15                  20                  25

GTC TAC AGA GCT GAG TCC ATA CAC ACT GGT TTG GAA GTT GCA ATC AAA      328
Val Tyr Arg Ala Glu Ser Ile His Thr Gly Leu Glu Val Ala Ile Lys
             30                  35                  40

ATG ATA GAT AAG AAA GCC ATG TAC AAA GCT GGA ATG GTA CAG AGA GTC      376
Met Ile Asp Lys Lys Ala Met Tyr Lys Ala Gly Met Val Gln Arg Val
                 45                  50                  55

CAA AAT GAG GTG AAA ATA CAT TGC CAG TTG AAA CAC CCC TCT GTC TTG      424
Gln Asn Glu Val Lys Ile His Cys Gln Leu Lys His Pro Ser Val Leu
         60                  65                  70

GAG CTC TAT AAT TAC TTT GAA GAT AAC AAT TAT GTC TAC CTG GTA TTG      472
Glu Leu Tyr Asn Tyr Phe Glu Asp Asn Asn Tyr Val Tyr Leu Val Leu
     75                  80                  85

GAA ATG TGC CAC AAT GGA GAA ATG AAC AGA TAT CTG AAG AAC AGA ATG      520
Glu Met Cys His Asn Gly Glu Met Asn Arg Tyr Leu Lys Asn Arg Met
 90                  95                 100                 105

AAG CCT TTC TCA GAA AGG GAA GCT AGG CAC TTC ATG CAC CAG ATT ATC      568
Lys Pro Phe Ser Glu Arg Glu Ala Arg His Phe Met His Gln Ile Ile
                110                 115                 120

ACA GGA ATG TTA TAT CTT CAT TCT CAT GGC ATA TTG CAC CGG GAC CTC      616
Thr Gly Met Leu Tyr Leu His Ser His Gly Ile Leu His Arg Asp Leu
            125                 130                 135

ACA CTC TCT AAC ATC TTA CTT ACG CGG AAT ATG AAC ATA AAA ATT GCT      664
Thr Leu Ser Asn Ile Leu Leu Thr Arg Asn Met Asn Ile Lys Ile Ala
        140                 145                 150

GAC TTT GGA CTA GCA ACG CAG TTG AAT ATG CCA CAT GAA AAG CAC TAT      712
Asp Phe Gly Leu Ala Thr Gln Leu Asn Met Pro His Glu Lys His Tyr
    155                 160                 165

ACA CTC TGT GGG ACT CCT AAT TAT ATT TCA CCA GAA ATT GCA ACT CGA      760
Thr Leu Cys Gly Thr Pro Asn Tyr Ile Ser Pro Glu Ile Ala Thr Arg
170                 175                 180                 185

AGT GCA CAT GGA CTT GAA TCT GAT ATT TGG TCA TTG GGC TGT ATG TCT      808
Ser Ala His Gly Leu Glu Ser Asp Ile Trp Ser Leu Gly Cys Met Ser
                190                 195                 200

TAT ACG TTA CTT ATT GGA AGA CCA CCT TTT GAC ACT GAC ACA GTC AAG      856
Tyr Thr Leu Leu Ile Gly Arg Pro Pro Phe Asp Thr Asp Thr Val Lys
            205                 210                 215
```

| | | | | | | | | | | | | | | | |
|---|---|---|---|---|---|---|---|---|---|---|---|---|---|---|---|
|AAC|ACA|TTG|AAC|AAA|GTA|GTC|CTG|GCA|GAT|TAT|GAA|ATG|CCA|GCC|TTT|904
|Asn|Thr|Leu|Asn|Lys|Val|Val|Leu|Ala|Asp|Tyr|Glu|Met|Pro|Ala|Phe|
| |  |220|   |   |   |   |225|   |   |   |   |230|   |   |   |

```
AAC ACA TTG AAC AAA GTA GTC CTG GCA GAT TAT GAA ATG CCA GCC TTT          904
Asn Thr Leu Asn Lys Val Val Leu Ala Asp Tyr Glu Met Pro Ala Phe
        220                 225                 230

TTG TCA CGA GAG GCC CAG GAC CTT ATC CAC CAG TTA CTT CGT AGA AAC          952
Leu Ser Arg Glu Ala Gln Asp Leu Ile His Gln Leu Leu Arg Arg Asn
        235                 240                 245

CCT GCA GAT CGG TTA AGT CTG TCT TCT GTG TTG GAC CAT CCT TTC ATG         1000
Pro Ala Asp Arg Leu Ser Leu Ser Ser Val Leu Asp His Pro Phe Met
250                 255                 260                 265

TCA CGA AAT CCT TCA CCA AAG AGT AAA GAC GTA GGG ACT GTA GAG GAC         1048
Ser Arg Asn Pro Ser Pro Lys Ser Lys Asp Val Gly Thr Val Glu Asp
                270                 275                 280

TCA ATG GAT AGT GGG CAT GCT ACA CTT TCC ACA ACA ATT ACA GCC TCT         1096
Ser Met Asp Ser Gly His Ala Thr Leu Ser Thr Thr Ile Thr Ala Ser
        285                 290                 295

TCT GGT ACC AGT TTG AGT GGC AGC CTA CTT GAC AGA AGA CTT TTG GTT         1144
Ser Gly Thr Ser Leu Ser Gly Ser Leu Leu Asp Arg Arg Leu Leu Val
        300                 305                 310

GGT CAA CCA CTT CCA AAT AAA ATT ACT GTA TTT CAA AAA AAT AAA AAT         1192
Gly Gln Pro Leu Pro Asn Lys Ile Thr Val Phe Gln Lys Asn Lys Asn
        315                 320                 325

TCA AGT GAC TTT TCT TCA GGA GAT GGA AGT AAT TTT TGT ACT CAA TGG         1240
Ser Ser Asp Phe Ser Ser Gly Asp Gly Ser Asn Phe Cys Thr Gln Trp
330                 335                 340                 345

GGA AAT CCA GAA CAA GAA GCT AAT AGT AGG GGA CGG GGG AGA GTG ATT         1288
Gly Asn Pro Glu Gln Glu Ala Asn Ser Arg Gly Arg Gly Arg Val Ile
                350                 355                 360

GAA GAT GCA GAA GAG AGG CCG CAT TCT CGA TAC CTG CGC AGA GCT CAT         1336
Glu Asp Ala Glu Glu Arg Pro His Ser Arg Tyr Leu Arg Arg Ala His
        365                 370                 375

TCC TCT GAT AGA GCC AGC CCC TCT AAT CAG TCT CGA GCA AAA ACA TAC         1384
Ser Ser Asp Arg Ala Ser Pro Ser Asn Gln Ser Arg Ala Lys Thr Tyr
        380                 385                 390

TCA GTA GAA CGT TGT CAC TCA GTA GAA ATG CTT TCA AAG CCT AGA AGA         1432
Ser Val Glu Arg Cys His Ser Val Glu Met Leu Ser Lys Pro Arg Arg
        395                 400                 405

TCA CTG GAT GAA AAT CAA CAC                                             1453
Ser Leu Asp Glu Asn Gln His
410                 415

(2) INFORMATION FOR SEQ ID NO:2:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Cys Ile Gly Glu Arg Ile Glu Asp Phe Lys Val Gly Asn
 1               5                  10                  15

Leu Leu Gly Lys Gly Ser Phe Ala Gly Val Tyr Arg Ala Glu Ser Ile
                20                  25                  30

His Thr Gly Leu Glu Val Ala Ile Lys Met Ile Asp Lys Lys Ala Met
        35                  40                  45

Tyr Lys Ala Gly Met Val Gln Arg Val Gln Asn Glu Val Lys Ile His
 50                  55                  60

Cys Gln Leu Lys His Pro Ser Val Leu Glu Leu Tyr Asn Tyr Phe Glu
 65                  70                  75                  80

Asp Asn Asn Tyr Val Tyr Leu Val Leu Glu Met Cys His Asn Gly Glu
```

```
                        85                  90                  95
Met Asn Arg Tyr Leu Lys Asn Arg Met Lys Pro Phe Ser Glu Arg Glu
                100                 105                 110

Ala Arg His Phe Met His Gln Ile Ile Thr Gly Met Leu Tyr Leu His
            115                 120                 125

Ser His Gly Ile Leu His Arg Asp Leu Thr Leu Ser Asn Ile Leu Leu
        130                 135                 140

Thr Arg Asn Met Asn Ile Lys Ile Ala Asp Phe Gly Leu Ala Thr Gln
145                 150                 155                 160

Leu Asn Met Pro His Glu Lys His Tyr Thr Leu Cys Gly Thr Pro Asn
                165                 170                 175

Tyr Ile Ser Pro Glu Ile Ala Thr Arg Ser Ala His Gly Leu Glu Ser
            180                 185                 190

Asp Ile Trp Ser Leu Gly Cys Met Ser Tyr Thr Leu Leu Ile Gly Arg
        195                 200                 205

Pro Pro Phe Asp Thr Asp Thr Val Lys Asn Thr Leu Asn Lys Val Val
    210                 215                 220

Leu Ala Asp Tyr Glu Met Pro Ala Phe Leu Ser Arg Glu Ala Gln Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Pro Ser Pro Lys
            260                 265                 270

Ser Lys Asp Val Gly Thr Val Glu Asp Ser Met Asp Ser Gly His Ala
        275                 280                 285

Thr Leu Ser Thr Thr Ile Thr Ala Ser Ser Gly Thr Ser Leu Ser Gly
        290                 295                 300

Ser Leu Leu Asp Arg Arg Leu Leu Val Gly Gln Pro Leu Pro Asn Lys
305                 310                 315                 320

Ile Thr Val Phe Gln Lys Asn Lys Asn Ser Ser Asp Phe Ser Ser Gly
                325                 330                 335

Asp Gly Ser Asn Phe Cys Thr Gln Trp Gly Asn Pro Glu Gln Glu Ala
            340                 345                 350

Asn Ser Arg Gly Arg Gly Arg Val Ile Glu Asp Ala Glu Glu Arg Pro
        355                 360                 365

His Ser Arg Tyr Leu Arg Arg Ala His Ser Ser Asp Arg Ala Ser Pro
    370                 375                 380

Ser Asn Gln Ser Arg Ala Lys Thr Tyr Ser Val Glu Arg Cys His Ser
385                 390                 395                 400

Val Glu Met Leu Ser Lys Pro Arg Arg Ser Leu Asp Glu Asn Gln His
                405                 410                 415

(2) INFORMATION FOR SEQ ID NO:3:

(i) SEQUENCE CHARACTERISTICS:
        (A) LENGTH: 3447 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mus musculus
        (D) DEVELOPMENTAL STAGE: Lymphoid cDNA Library (vii) IMMEDIATE SOURCE:
        (A) LIBRARY: Murine Lymphoid
        (B) CLONE: WGA-resistant chop clones
```

-continued (ix) FEATURE:
   (A) NAME/KEY: 5'UTR
   (B) LOCATION: 1..205

(ix) FEATURE:
   (A) NAME/KEY: CDS
   (B) LOCATION: 206..2980

(ix) FEATURE:
   (A) NAME/KEY: 3'UTR
   (B) LOCATION: 2981..3447

(xi) SEQUENCE DESCRIPTION: SEQ ID NO:3:

```
GCGGGAATTT TCAAAATGG GAGCTCCGGG GCGCCGCCCA GGCCTCGGGA GGTACCGGGG         60

GTACCTTTCG GTGGCGTTGG CGGCGTCGCC AGCGGCGGCG TAGAGAAGGC GTCCTGATGG        120

GCGCCAAGAC CTGCTGGCTT CTCGGAGCGC TGCCTCGGAG GGGACTGCGA AAGGCCGAG         180

CCCCGGGCGC CGGCGGCTCG GGAAC ATG GCG GCG TGC ATC GGG GAG AGG ATC         232
                            Met Ala Ala Cys Ile Gly Glu Arg Ile
                             1               5

GAG GAC TTT AAG GTT GGA AAT CTA CTC GGT AAA GGA TCA TTT GCT GGT         280
Glu Asp Phe Lys Val Gly Asn Leu Leu Gly Lys Gly Ser Phe Ala Gly
 10              15                  20                  25

GTC TAC AGA GCT GAG TCC ATA CAC ACT GGT TTG GAA GTT GCA ATC AAA         328
Val Tyr Arg Ala Glu Ser Ile His Thr Gly Leu Glu Val Ala Ile Lys
             30                  35                  40

ATG ATA GAT AAG AAA GCC ATG TAC AAA GCT GGA ATG GTA CAG AGA GTC         376
Met Ile Asp Lys Lys Ala Met Tyr Lys Ala Gly Met Val Gln Arg Val
         45                  50                  55

CAA AAT GAG GTG AAA ATA CAT TGC CAG TTG AAA CAC CCC TCT GTC TTG         424
Gln Asn Glu Val Lys Ile His Cys Gln Leu Lys His Pro Ser Val Leu
     60                  65                  70

GAG CTC TAT AAT TAC TTT GAA GAT AAC AAT TAT GTC TAC CTG GTA TTG         472
Glu Leu Tyr Asn Tyr Phe Glu Asp Asn Asn Tyr Val Tyr Leu Val Leu
 75                  80                  85

GAA ATG TGC CAC AAT GGA GAA ATG AAC AGA TAT CTG AAG AAC AGA ATG         520
Glu Met Cys His Asn Gly Glu Met Asn Arg Tyr Leu Lys Asn Arg Met
 90                  95                 100                 105

AAG CCT TTC TCA GAA AGG GAA GCT AGG CAC TTC ATG CAC CAG ATT ATC         568
Lys Pro Phe Ser Glu Arg Glu Ala Arg His Phe Met His Gln Ile Ile
             110                 115                 120

ACA GGA ATG TTA TAT CTT CAT TCT CAT GGC ATA TTG CAC CGG GAC CTC         616
Thr Gly Met Leu Tyr Leu His Ser His Gly Ile Leu His Arg Asp Leu
         125                 130                 135

ACA CTC TCT AAC ATC TTA CTT ACG CGG AAT ATG AAC ATA AAA ATT GCT         664
Thr Leu Ser Asn Ile Leu Leu Thr Arg Asn Met Asn Ile Lys Ile Ala
     140                 145                 150

GAC TTT GGA CTA GCA ACG CAG TTG AAT ATG CCA CAT GAA AAG CAC TAT         712
Asp Phe Gly Leu Ala Thr Gln Leu Asn Met Pro His Glu Lys His Tyr
 155                 160                 165

ACA CTC TGT GGG ACT CCT AAT TAT ATT TCA CCA GAA ATT GCA ACT CGA         760
Thr Leu Cys Gly Thr Pro Asn Tyr Ile Ser Pro Glu Ile Ala Thr Arg
170                 175                 180                 185

AGT GCA CAT GGA CTT GAA TCT GAT ATT TGG TCA TTG GGC TGT ATG TCT         808
Ser Ala His Gly Leu Glu Ser Asp Ile Trp Ser Leu Gly Cys Met Ser
             190                 195                 200

TAT ACG TTA CTT ATT GGA AGA CCA CCT TTT GAC ACT GAC ACA GTC AAG         856
Tyr Thr Leu Leu Ile Gly Arg Pro Pro Phe Asp Thr Asp Thr Val Lys
         205                 210                 215

AAC ACA TTG AAC AAA GTA GTC CTG GCA GAT TAT GAA ATG CCA GCC TTT         904
Asn Thr Leu Asn Lys Val Val Leu Ala Asp Tyr Glu Met Pro Ala Phe
     220                 225                 230
```

```
                                                         -continued

TTG TCA CGA GAG GCC CAG GAC CTT ATC CAC CAG TTA CTT CGT AGA AAC      952
Leu Ser Arg Glu Ala Gln Asp Leu Ile His Gln Leu Leu Arg Arg Asn
    235                 240                 245

CCT GCA GAT CGG TTA AGT CTG TCT TCT GTG TTG GAC CAT CCT TTC ATG     1000
Pro Ala Asp Arg Leu Ser Leu Ser Ser Val Leu Asp His Pro Phe Met
250                 255                 260                 265

TCA CGA AAT CCT TCA CCA AAG AGT AAA GAC GTA GGG ACT GTA GAG GAC     1048
Ser Arg Asn Pro Ser Pro Lys Ser Lys Asp Val Gly Thr Val Glu Asp
                270                 275                 280

TCA ATG GAT AGT GGG CAT GCT ACA CTT TCC ACA ACA ATT ACA GCC TCT     1096
Ser Met Asp Ser Gly His Ala Thr Leu Ser Thr Thr Ile Thr Ala Ser
        285                 290                 295

TCT GGT ACC AGT TTG AGT GGC AGC CTA CTT GAC AGA AGA CTT TTG GTT     1144
Ser Gly Thr Ser Leu Ser Gly Ser Leu Leu Asp Arg Arg Leu Leu Val
                300                 305                 310

GGT CAA CCA CTT CCA AAT AAA ATT ACT GTA TTT CAA AAA AAT AAA AAT     1192
Gly Gln Pro Leu Pro Asn Lys Ile Thr Val Phe Gln Lys Asn Lys Asn
315                 320                 325

TCA AGT GAC TTT TCT TCA GGA GAT GGA AGT AAT TTT TGT ACT CAA TGG     1240
Ser Ser Asp Phe Ser Ser Gly Asp Gly Ser Asn Phe Cys Thr Gln Trp
330                 335                 340                 345

GGA AAT CCA GAA CAA GAA GCT AAT AGT AGG GGA CGG GGG AGA GTG ATT     1288
Gly Asn Pro Glu Gln Glu Ala Asn Ser Arg Gly Arg Gly Arg Val Ile
                350                 355                 360

GAA GAT GCA GAA GAG AGG CCG CAT TCT CGA TAC CTG CGC AGA GCT CAT     1336
Glu Asp Ala Glu Glu Arg Pro His Ser Arg Tyr Leu Arg Arg Ala His
        365                 370                 375

TCC TCT GAT AGA GCC AGC CCC TCT AAT CAG TCT CGA GCA AAA ACA TAC     1384
Ser Ser Asp Arg Ala Ser Pro Ser Asn Gln Ser Arg Ala Lys Thr Tyr
    380                 385                 390

TCA GTA GAA CGT TGT CAC TCA GTA GAA ATG CTT TCA AAG CCT AGA AGA     1432
Ser Val Glu Arg Cys His Ser Val Glu Met Leu Ser Lys Pro Arg Arg
395                 400                 405

TCA CTG GAT GAA AAT CAA CAC AGT TCC AAT CAT CAT TGT CTA GGA AAA     1480
Ser Leu Asp Glu Asn Gln His Ser Ser Asn His His Cys Leu Gly Lys
410                 415                 420                 425

ACT CCT TTT CCA TTT GCA GAC CAG ACA CCT CAG ATG GAA ATG GTA CAG     1528
Thr Pro Phe Pro Phe Ala Asp Gln Thr Pro Gln Met Glu Met Val Gln
                430                 435                 440

CAG TGG TTT GGG AAT CTG CAA ATG AAT GCT CAT TTA GGA GAA ACT AAT     1576
Gln Trp Phe Gly Asn Leu Gln Met Asn Ala His Leu Gly Glu Thr Asn
        445                 450                 455

GAG CAC CAC ACC GTT AGC CCA AAC AGA GAT TTC CAG GAC TAT CCA GAT     1624
Glu His His Thr Val Ser Pro Asn Arg Asp Phe Gln Asp Tyr Pro Asp
    460                 465                 470

TTG CAG GAC ACG TTA CGA AAC GCT TGG ACT GAC ACG AGA GCC AGC AAG     1672
Leu Gln Asp Thr Leu Arg Asn Ala Trp Thr Asp Thr Arg Ala Ser Lys
475                 480                 485

AAT GCT GAT ACT TCT GCC AAT GTT CAT GCT GTA AAG CAG CTG AGT GCC     1720
Asn Ala Asp Thr Ser Ala Asn Val His Ala Val Lys Gln Leu Ser Ala
490                 495                 500                 505

ATG AAA TAC ATG AGT GCA CAT CAC CAT AAG CCT GAG GTC ATG CCA CAG     1768
Met Lys Tyr Met Ser Ala His His His Lys Pro Glu Val Met Pro Gln
                510                 515                 520

GAG CCG GGC CTA CAT CCT CAT TCT GAA CAA AGC AAG AAT AGA AGT ATG     1816
Glu Pro Gly Leu His Pro His Ser Glu Gln Ser Lys Asn Arg Ser Met
        525                 530                 535

GAG TCG ACA CTG GGT TAC CAG AAA CCT ACC TTA AGA AGT ATT ACA TCT     1864
Glu Ser Thr Leu Gly Tyr Gln Lys Pro Thr Leu Arg Ser Ile Thr Ser
    540                 545                 550
```

-continued

| | |
|---|---|
| CCT CTG ATT GCT CAC AGA TTA AAG CCA ATC AGA CAG AAA ACC AAA AAG<br>Pro Leu Ile Ala His Arg Leu Lys Pro Ile Arg Gln Lys Thr Lys Lys<br>555 560 565 | 1912 |
| GCT GTG GTG AGC ATC CTT GAT TCA GAG GAG GTG TGT GTG GAG CTT CTG<br>Ala Val Val Ser Ile Leu Asp Ser Glu Glu Val Cys Val Glu Leu Leu<br>570 575 580 585 | 1960 |
| AGA GAG TGT GCG TCT GAA GGA TAT GTG AAA GAA GTG CTT CAG ATA TCG<br>Arg Glu Cys Ala Ser Glu Gly Tyr Val Lys Glu Val Leu Gln Ile Ser<br>590 595 600 | 2008 |
| AGT GAT GGG ACT ATG ATC ACT GTT TAT TAC CCG AAC GAT GGA AGA GGC<br>Ser Asp Gly Thr Met Ile Thr Val Tyr Tyr Pro Asn Asp Gly Arg Gly<br>605 610 615 | 2056 |
| TTT CCT CTT GCT GAC AGA CCT CCC TTG CCT ACT GAC AAC ATC AGT AGG<br>Phe Pro Leu Ala Asp Arg Pro Pro Leu Pro Thr Asp Asn Ile Ser Arg<br>620 625 630 | 2104 |
| TAC AGC TTT GAC AAT CTA CCA GAA AAA TAC TGG CGG AAA TAT CAG TAT<br>Tyr Ser Phe Asp Asn Leu Pro Glu Lys Tyr Trp Arg Lys Tyr Gln Tyr<br>635 640 645 | 2152 |
| GCT TCC AGA TTC ATT CAG CTA GTA AGA TCT AAA ACT CCC AAA ATC ACT<br>Ala Ser Arg Phe Ile Gln Leu Val Arg Ser Lys Thr Pro Lys Ile Thr<br>650 655 660 665 | 2200 |
| TAT TTT ACA AGA TAT GCT AAA TGT ATT TTG ATG GAA AAT TCT CCT GGT<br>Tyr Phe Thr Arg Tyr Ala Lys Cys Ile Leu Met Glu Asn Ser Pro Gly<br>670 675 680 | 2248 |
| GCT GAT TTC GAA GTT TGG TTT TAT GAT GGA GCC AAA ATA CAT AAA ACT<br>Ala Asp Phe Glu Val Trp Phe Tyr Asp Gly Ala Lys Ile His Lys Thr<br>685 690 695 | 2296 |
| GAA AAT TTA ATT CAC ATA ATT GAG AAA ACA GGG ATA TCT TAT AAT TTA<br>Glu Asn Leu Ile His Ile Ile Glu Lys Thr Gly Ile Ser Tyr Asn Leu<br>700 705 710 | 2344 |
| AAA AAT GAA AAT GAA GTT ACC AGC CTG AAA GAG GAA GTA AAA GTA TAT<br>Lys Asn Glu Asn Glu Val Thr Ser Leu Lys Glu Glu Val Lys Val Tyr<br>715 720 725 | 2392 |
| ATG GAC CAT GCT AAT GAG GGT CAC CGT ATT TGC TTG TCA CTG GAA TCT<br>Met Asp His Ala Asn Glu Gly His Arg Ile Cys Leu Ser Leu Glu Ser<br>730 735 740 745 | 2440 |
| GTA ATC TCT GAG GAG GAA AAG AGA AGC AGG GGT TCT TCA TTC TTC CCT<br>Val Ile Ser Glu Glu Glu Lys Arg Ser Arg Gly Ser Ser Phe Phe Pro<br>750 755 760 | 2488 |
| ATA ATC GTA GGA AGA AAA CCT GGT AAT ACT AGT TCA CCT AAA GCC TTA<br>Ile Ile Val Gly Arg Lys Pro Gly Asn Thr Ser Ser Pro Lys Ala Leu<br>765 770 775 | 2536 |
| TCA GCT CCT CCT GTG GAC CCA AGC TGC TGT AAG GGA GAG CAG GCG TCA<br>Ser Ala Pro Pro Val Asp Pro Ser Cys Cys Lys Gly Glu Gln Ala Ser<br>780 785 790 | 2584 |
| GCA AGC AGA CTG AGC GTG AAT AGT GCC GCT TTC CCC ACA CAG TCC CCA<br>Ala Ser Arg Leu Ser Val Asn Ser Ala Ala Phe Pro Thr Gln Ser Pro<br>795 800 805 | 2632 |
| GGA CTC AGT CCT TCC ACT GTG ACA GTT GAA GGA CTT GGC CAC ACA GCG<br>Gly Leu Ser Pro Ser Thr Val Thr Val Glu Gly Leu Gly His Thr Ala<br>810 815 820 825 | 2680 |
| ACT GCC ACA GGA ACA GGC GTC TCT TCA AGT CTT CCT AAA TCT GCA CAG<br>Thr Ala Thr Gly Thr Gly Val Ser Ser Ser Leu Pro Lys Ser Ala Gln<br>830 835 840 | 2728 |
| CTT TTG AAA TCT GTT TTT GTG AAA AAT GTT GGT TGG GCT ACA CAG CTA<br>Leu Leu Lys Ser Val Phe Val Lys Asn Val Gly Trp Ala Thr Gln Leu<br>845 850 855 | 2776 |
| ACT AGC GGA GCT GTG TGG GTT CAG TTT AAT GAT GGG TCA CAG TTG GTT<br>Thr Ser Gly Ala Val Trp Val Gln Phe Asn Asp Gly Ser Gln Leu Val<br>860 865 870 | 2824 |

-continued

```
GTC CAG GCA GGA GTA TCT TCC ATC AGT TAC ACA TCA CCA GAT GGT CAG      2872
Val Gln Ala Gly Val Ser Ser Ile Ser Tyr Thr Ser Pro Asp Gly Gln
    875                 880                 885

ACA ACT AGG TAT GGA GAA AAT GAA AAA TTA CCT GAA TAC ATC AAA CAG      2920
Thr Thr Arg Tyr Gly Glu Asn Glu Lys Leu Pro Glu Tyr Ile Lys Gln
890                 895                 900                 905

AAA TTA CAG TGT CTT TCT TCC ATC CTT CTG ATG TTT TCT AAT CCA ACT      2968
Lys Leu Gln Cys Leu Ser Ser Ile Leu Leu Met Phe Ser Asn Pro Thr
                910                 915                 920

CCT AAT TTT CAG TAATTTAAGT CTCAGAAGTC TATATTTAAT AAATGACTTT          3020
Pro Asn Phe Gln
            925

TTGGCTGGCT TTCAAGTAAG TGATTTTTTA AATTTACTTT AACTTCAGAA AGCCTTTCTA    3080

TTAAACAGAA TTTTAATATA CACAATAAAA ATATAATAAG AAAACAATAA AATTTCAGTT    3140

ACCTAATATA GTGGTCATAA GGCTAGGACA TCTAATTTTG CTCCAAGCAT GTAATCCTTC    3200

AAAGTTTGTG CTCCTATGTT TGTATTGAAC TAAGTTGTGT ATGGCTTGTT TGTTTTTGTT    3260

ATTTTCTTTA CTAATAAGAC ATTGAGAATC ACGGACAAAA CATAGTTTTC AATTTTTGAA    3320

TGTGTAAATA ATGTATTATA AGCAATATGT AAATGTGTAT ATTTTATATT TATTTTTATA    3380

GCACTTGTGT CTGATAAGAT TTCTGCAAAT ACATTTTATA AAATAAACAC AGTGGTAAGT    3440

TTTCCTT                                                              3447
```

(2) INFORMATION FOR SEQ ID NO:4:

(i) SEQUENCE CHARACTERISTICS:
        (A) LENGTH: 925 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ala Cys Ile Gly Glu Arg Ile Glu Asp Phe Lys Val Gly Asn
1               5                   10                  15

Leu Leu Gly Lys Gly Ser Phe Ala Gly Val Tyr Arg Ala Glu Ser Ile
                20                  25                  30

His Thr Gly Leu Glu Val Ala Ile Lys Met Ile Asp Lys Lys Ala Met
            35                  40                  45

Tyr Lys Ala Gly Met Val Gln Arg Val Gln Asn Glu Val Lys Ile His
        50                  55                  60

Cys Gln Leu Lys His Pro Ser Val Leu Glu Leu Tyr Asn Tyr Phe Glu
65                  70                  75                  80

Asp Asn Asn Tyr Val Tyr Leu Val Leu Glu Met Cys His Asn Gly Glu
                85                  90                  95

Met Asn Arg Tyr Leu Lys Asn Arg Met Lys Pro Phe Ser Glu Arg Glu
                100                 105                 110

Ala Arg His Phe Met His Gln Ile Ile Thr Gly Met Leu Tyr Leu His
            115                 120                 125

Ser His Gly Ile Leu His Arg Asp Leu Thr Leu Ser Asn Ile Leu Leu
        130                 135                 140

Thr Arg Asn Met Asn Ile Lys Ile Ala Asp Phe Gly Leu Ala Thr Gln
145                 150                 155                 160

Leu Asn Met Pro His Glu Lys His Tyr Thr Leu Cys Gly Thr Pro Asn
                165                 170                 175

Tyr Ile Ser Pro Glu Ile Ala Thr Arg Ser Ala His Gly Leu Glu Ser
                180                 185                 190
```

-continued

```
Asp Ile Trp Ser Leu Gly Cys Met Ser Tyr Thr Leu Leu Ile Gly Arg
            195                 200                 205

Pro Pro Phe Asp Thr Asp Thr Val Lys Asn Thr Leu Asn Lys Val Val
210                 215                 220

Leu Ala Asp Tyr Glu Met Pro Ala Phe Leu Ser Arg Glu Ala Gln Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Pro Ser Pro Lys
            260                 265                 270

Ser Lys Asp Val Gly Thr Val Glu Asp Ser Met Asp Ser Gly His Ala
            275                 280                 285

Thr Leu Ser Thr Thr Ile Thr Ala Ser Ser Gly Thr Ser Leu Ser Gly
            290                 295                 300

Ser Leu Leu Asp Arg Arg Leu Leu Val Gly Gln Pro Leu Pro Asn Lys
305                 310                 315                 320

Ile Thr Val Phe Gln Lys Asn Lys Asn Ser Ser Asp Phe Ser Ser Gly
                325                 330                 335

Asp Gly Ser Asn Phe Cys Thr Gln Trp Gly Asn Pro Glu Gln Glu Ala
            340                 345                 350

Asn Ser Arg Gly Arg Gly Arg Val Ile Glu Asp Ala Glu Glu Arg Pro
            355                 360                 365

His Ser Arg Tyr Leu Arg Arg Ala His Ser Ser Asp Arg Ala Ser Pro
            370                 375                 380

Ser Asn Gln Ser Arg Ala Lys Thr Tyr Ser Val Glu Arg Cys His Ser
385                 390                 395                 400

Val Glu Met Leu Ser Lys Pro Arg Arg Ser Leu Asp Glu Asn Gln His
                405                 410                 415

Ser Ser Asn His His Cys Leu Gly Lys Thr Pro Phe Pro Phe Ala Asp
            420                 425                 430

Gln Thr Pro Gln Met Glu Met Val Gln Gln Trp Phe Gly Asn Leu Gln
            435                 440                 445

Met Asn Ala His Leu Gly Glu Thr Asn Glu His His Thr Val Ser Pro
450                 455                 460

Asn Arg Asp Phe Gln Asp Tyr Pro Asp Leu Gln Asp Thr Leu Arg Asn
465                 470                 475                 480

Ala Trp Thr Asp Thr Arg Ala Ser Lys Asn Ala Asp Thr Ser Ala Asn
                485                 490                 495

Val His Ala Val Lys Gln Leu Ser Ala Met Lys Tyr Met Ser Ala His
            500                 505                 510

His His Lys Pro Glu Val Met Pro Gln Glu Pro Gly Leu His Pro His
            515                 520                 525

Ser Glu Gln Ser Lys Asn Arg Ser Met Glu Ser Thr Leu Gly Tyr Gln
530                 535                 540

Lys Pro Thr Leu Arg Ser Ile Thr Ser Pro Leu Ile Ala His Arg Leu
545                 550                 555                 560

Lys Pro Ile Arg Gln Lys Thr Lys Ala Val Val Ser Ile Leu Asp
                565                 570                 575

Ser Glu Glu Val Cys Val Glu Leu Leu Arg Glu Cys Ala Ser Glu Gly
            580                 585                 590

Tyr Val Lys Glu Val Leu Gln Ile Ser Ser Asp Gly Thr Met Ile Thr
            595                 600                 605

Val Tyr Tyr Pro Asn Asp Gly Arg Gly Phe Pro Leu Ala Asp Arg Pro
```

```
            610                615                620
Pro Leu Pro Thr Asp Asn Ile Ser Arg Tyr Ser Phe Asp Asn Leu Pro
625                 630                 635                 640

Glu Lys Tyr Trp Arg Lys Tyr Gln Tyr Ala Ser Arg Phe Ile Gln Leu
                645                 650                 655

Val Arg Ser Lys Thr Pro Lys Ile Thr Tyr Phe Thr Arg Tyr Ala Lys
                660                 665                 670

Cys Ile Leu Met Glu Asn Ser Pro Gly Ala Asp Phe Glu Val Trp Phe
            675                 680                 685

Tyr Asp Gly Ala Lys Ile His Lys Thr Glu Asn Leu Ile His Ile Ile
690                 695                 700

Glu Lys Thr Gly Ile Ser Tyr Asn Leu Lys Asn Glu Asn Glu Val Thr
705                 710                 715                 720

Ser Leu Lys Glu Glu Val Lys Val Tyr Met Asp His Ala Asn Glu Gly
                725                 730                 735

His Arg Ile Cys Leu Ser Leu Glu Ser Val Ile Ser Glu Glu Glu Lys
                740                 745                 750

Arg Ser Arg Gly Ser Ser Phe Phe Pro Ile Ile Val Gly Arg Lys Pro
                755                 760                 765

Gly Asn Thr Ser Ser Pro Lys Ala Leu Ser Ala Pro Pro Val Asp Pro
770                 775                 780

Ser Cys Cys Lys Gly Glu Gln Ala Ser Ala Ser Arg Leu Ser Val Asn
785                 790                 795                 800

Ser Ala Ala Phe Pro Thr Gln Ser Pro Gly Leu Ser Pro Ser Thr Val
                805                 810                 815

Thr Val Glu Gly Leu Gly His Thr Ala Thr Ala Thr Gly Thr Gly Val
                820                 825                 830

Ser Ser Ser Leu Pro Lys Ser Ala Gln Leu Leu Lys Ser Val Phe Val
                835                 840                 845

Lys Asn Val Gly Trp Ala Thr Gln Leu Thr Ser Gly Ala Val Trp Val
850                 855                 860

Gln Phe Asn Asp Gly Ser Gln Leu Val Val Gln Ala Gly Val Ser Ser
865                 870                 875                 880

Ile Ser Tyr Thr Ser Pro Asp Gly Gln Thr Thr Arg Tyr Gly Glu Asn
                885                 890                 895

Glu Lys Leu Pro Glu Tyr Ile Lys Gln Lys Leu Gln Cys Leu Ser Ser
                900                 905                 910

Ile Leu Leu Met Phe Ser Asn Pro Thr Pro Asn Phe Gln
            915                 920                 925

(2) INFORMATION FOR SEQ ID NO:5:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mus musculus
        (D) DEVELOPMENTAL STAGE: Lymphoid cDNA Library (vii) IMMEDIATE SOURCE:
        (A) LIBRARY: Murine Lymphoid
        (B) CLONE: WGA-resistant chop clones (ix) FEATURE:
        (A) NAME/KEY: 5'UTR
```

(B) LOCATION: 1..205

(ix) FEATURE:
        (A) NAME/KEY: CDS
        (B) LOCATION: 206..1597

(xi) SEQUENCE DESCRIPTION: SEQ ID NO:5:

```
GCGGGAATTT TTCAAAATGG GAGCTCCGGG GCGCCGCCCA GGCCTCGGGA GGTACCGGGG         60

GTACCTTTCG GTGGCGTTGG CGGCGTCGCC AGCGGCGGCG TAGAGAAGGC GTCCTGATGG        120

GCGCCAAGAC CTGCTGGCTT CTCGGAGCGC TGCCTCGGAG GGGACTGCGA GAAGGCCGAG        180

CCCCGGGCGC CGGCGGCTCG GGAAC ATG GCG GCG TGC ATC GGG GAG AGG ATC         232
                              Met Ala Ala Cys Ile Gly Glu Arg Ile
                               1               5

GAG GAC TTT AAG GTT GGA AAT CTA CTC GGT AAA GGA TCA TTT GCT GGT         280
Glu Asp Phe Lys Val Gly Asn Leu Leu Gly Lys Gly Ser Phe Ala Gly
 10              15                  20                  25

GTC TAC AGA GCT GAG TCC ATA CAC ACT GGT TTG GAA GTT GCA ATC AAA         328
Val Tyr Arg Ala Glu Ser Ile His Thr Gly Leu Glu Val Ala Ile Lys
             30                  35                  40

ATG ATA GAT AAG AAA GCC ATG TAC AAA GCT GGA ATG GTA CAG AGA GTC         376
Met Ile Asp Lys Lys Ala Met Tyr Lys Ala Gly Met Val Gln Arg Val
         45                  50                  55

CAA AAT GAG GTG AAA ATA CAT TGC CAG TTG AAA CAC CCC TCT GTC TTG         424
Gln Asn Glu Val Lys Ile His Cys Gln Leu Lys His Pro Ser Val Leu
     60                  65                  70

GAG CTC TAT AAT TAC TTT GAA GAT AAC AAT TAT GTC TAC CTG GTA TTG         472
Glu Leu Tyr Asn Tyr Phe Glu Asp Asn Asn Tyr Val Tyr Leu Val Leu
 75                  80                  85

GAA ATG TGC CAC AAT GGA GAA ATG AAC AGA TAT CTG AAG AAC AGA ATG         520
Glu Met Cys His Asn Gly Glu Met Asn Arg Tyr Leu Lys Asn Arg Met
 90                  95                 100                 105

AAG CCT TTC TCA GAA AGG GAA GCT AGG CAC TTC ATG CAC CAG ATT ATC         568
Lys Pro Phe Ser Glu Arg Glu Ala Arg His Phe Met His Gln Ile Ile
                110                 115                 120

ACA GGA ATG TTA TAT CTT CAT TCT CAT GGC ATA TTG CAC CGG GAC CTC         616
Thr Gly Met Leu Tyr Leu His Ser His Gly Ile Leu His Arg Asp Leu
            125                 130                 135

ACA CTC TCT AAC ATC TTA CTT ACG CGG AAT ATG AAC ATA AAA ATT GCT         664
Thr Leu Ser Asn Ile Leu Leu Thr Arg Asn Met Asn Ile Lys Ile Ala
        140                 145                 150

GAC TTT GGA CTA GCA ACG CAG TTG AAT ATG CCA CAT GAA AAG CAC TAT         712
Asp Phe Gly Leu Ala Thr Gln Leu Asn Met Pro His Glu Lys His Tyr
    155                 160                 165

ACA CTC TGT GGG ACT CCT AAT TAT ATT TCA CCA GAA ATT GCA ACT CGA         760
Thr Leu Cys Gly Thr Pro Asn Tyr Ile Ser Pro Glu Ile Ala Thr Arg
170                 175                 180                 185

AGT GCA CAT GGA CTT GAA TCT GAT ATT TGG TCA TTG GGC TGT ATG TCT         808
Ser Ala His Gly Leu Glu Ser Asp Ile Trp Ser Leu Gly Cys Met Ser
                190                 195                 200

TAT ACG TTA CTT ATT GGA AGA CCA CCT TTT GAC ACT GAC ACA GTC AAG         856
Tyr Thr Leu Leu Ile Gly Arg Pro Pro Phe Asp Thr Asp Thr Val Lys
            205                 210                 215

AAC ACA TTG AAC AAA GTA GTC CTG GCA GAT TAT GAA ATG CCA GCC TTT         904
Asn Thr Leu Asn Lys Val Val Leu Ala Asp Tyr Glu Met Pro Ala Phe
        220                 225                 230

TTG TCA CGA GAG GCC CAG GAC CTT ATC CAC CAG TTA CTT CGT AGA AAC         952
Leu Ser Arg Glu Ala Gln Asp Leu Ile His Gln Leu Leu Arg Arg Asn
    235                 240                 245

CCT GCA GAT CGG TTA AGT CTG TCT TCT GTG TTG GAC CAT CCT TTC ATG        1000
Pro Ala Asp Arg Leu Ser Leu Ser Ser Val Leu Asp His Pro Phe Met
```

```
                250                    255                    260                    265

TCA CGA AAT CCT TCA CCA AAG AGT AAA GAC GTA GGG ACT GTA GAG GAC        1048
Ser Arg Asn Pro Ser Pro Lys Ser Lys Asp Val Gly Thr Val Glu Asp
                    270                    275                    280

TCA ATG GAT AGT GGG CAT GCT ACA CTT TCC ACA ACA ATT ACA GCC TCT        1096
Ser Met Asp Ser Gly His Ala Thr Leu Ser Thr Thr Ile Thr Ala Ser
                285                    290                    295

TCT GGT ACC AGT TTG AGT GGC AGC CTA CTT GAC AGA AGA CTT TTG GTT        1144
Ser Gly Thr Ser Leu Ser Gly Ser Leu Leu Asp Arg Arg Leu Leu Val
            300                    305                    310

GGT CAA CCA CTT CCA AAT AAA ATT ACT GTA TTT CAA AAA AAT AAA AAT        1192
Gly Gln Pro Leu Pro Asn Lys Ile Thr Val Phe Gln Lys Asn Lys Asn
        315                    320                    325

TCA AGT GAC TTT TCT TCA GGA GAT GGA AGT AAT TTT TGT ACT CAA TGG        1240
Ser Ser Asp Phe Ser Ser Gly Asp Gly Ser Asn Phe Cys Thr Gln Trp
330                    335                    340                    345

GGA AAT CCA GAA CAA GAA GCT AAT AGT AGG GGA CGG GGG AGA GTG ATT        1288
Gly Asn Pro Glu Gln Glu Ala Asn Ser Arg Gly Arg Gly Arg Val Ile
                    350                    355                    360

GAA GAT GCA GAA GAG AGG CCG CAT TCT CGA TAC CTG CGC AGA GCT CAT        1336
Glu Asp Ala Glu Glu Arg Pro His Ser Arg Tyr Leu Arg Arg Ala His
                365                    370                    375

TCC TCT GAT AGA GCC AGC CCC TCT AAT CAG TCT CGA GCA AAA ACA TAC        1384
Ser Ser Asp Arg Ala Ser Pro Ser Asn Gln Ser Arg Ala Lys Thr Tyr
            380                    385                    390

TCA GTA GAA CGT TGT CAC TCA GTA GAA ATG CTT TCA AAG CCT AGA AGA        1432
Ser Val Glu Arg Cys His Ser Val Glu Met Leu Ser Lys Pro Arg Arg
        395                    400                    405

TCA CTG GAT GAA AAT CAA CAC AGG TAT TCA CCC ACC AAA AGC AAT GTC        1480
Ser Leu Asp Glu Asn Gln His Arg Tyr Ser Pro Thr Lys Ser Asn Val
410                    415                    420                    425

AAT GTT TTA ACT TCA TTA AAC ACC AAA CAG CCA ATA GTT AAG GAT CTT        1528
Asn Val Leu Thr Ser Leu Asn Thr Lys Gln Pro Ile Val Lys Asp Leu
                    430                    435                    440

TTG AAA GAC CGT ATA ATG ACT GAG CAG TAT AAG GAT AAT CTT TTA AAC        1576
Leu Lys Asp Arg Ile Met Thr Glu Gln Tyr Lys Asp Asn Leu Leu Asn
                445                    450                    455

TTA TTG AAC AAG TTT GAT CGC TAA                                        1600
Leu Leu Asn Lys Phe Asp Arg
            460

(2) INFORMATION FOR SEQ ID NO:6:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Ala Cys Ile Gly Glu Arg Ile Glu Asp Phe Lys Val Gly Asn
1                   5                   10                  15

Leu Leu Gly Lys Gly Ser Phe Ala Gly Val Tyr Arg Ala Glu Ser Ile
                20                  25                  30

His Thr Gly Leu Glu Val Ala Ile Lys Met Ile Asp Lys Lys Ala Met
            35                  40                  45

Tyr Lys Ala Gly Met Val Gln Arg Val Gln Asn Glu Val Lys Ile His
        50                  55                  60

Cys Gln Leu Lys His Pro Ser Val Leu Glu Leu Tyr Asn Tyr Phe Glu
65                  70                  75                  80
```

-continued

```
Asp Asn Asn Tyr Val Tyr Leu Val Leu Glu Met Cys His Asn Gly Glu
             85                  90                  95
Met Asn Arg Tyr Leu Lys Asn Arg Met Lys Pro Phe Ser Glu Arg Glu
            100                 105                 110
Ala Arg His Phe Met His Gln Ile Ile Thr Gly Met Leu Tyr Leu His
            115                 120                 125
Ser His Gly Ile Leu His Arg Asp Leu Thr Leu Ser Asn Ile Leu Leu
            130                 135                 140
Thr Arg Asn Met Asn Ile Lys Ile Ala Asp Phe Gly Leu Ala Thr Gln
145                 150                 155                 160
Leu Asn Met Pro His Glu Lys His Tyr Thr Leu Cys Gly Thr Pro Asn
            165                 170                 175
Tyr Ile Ser Pro Glu Ile Ala Thr Arg Ser Ala His Gly Leu Glu Ser
            180                 185                 190
Asp Ile Trp Ser Leu Gly Cys Met Ser Tyr Thr Leu Leu Ile Gly Arg
            195                 200                 205
Pro Pro Phe Asp Thr Asp Thr Val Lys Asn Thr Leu Asn Lys Val Val
210                 215                 220
Leu Ala Asp Tyr Glu Met Pro Ala Phe Leu Ser Arg Glu Ala Gln Asp
225                 230                 235                 240
Leu Ile His Gln Leu Leu Arg Arg Asn Pro Ala Asp Arg Leu Ser Leu
            245                 250                 255
Ser Ser Val Leu Asp His Pro Phe Met Ser Arg Asn Pro Ser Pro Lys
            260                 265                 270
Ser Lys Asp Val Gly Thr Val Glu Asp Ser Met Asp Ser Gly His Ala
            275                 280                 285
Thr Leu Ser Thr Thr Ile Thr Ala Ser Ser Gly Thr Ser Leu Ser Gly
            290                 295                 300
Ser Leu Leu Asp Arg Arg Leu Leu Val Gly Gln Pro Leu Pro Asn Lys
305                 310                 315                 320
Ile Thr Val Phe Gln Lys Asn Lys Asn Ser Ser Asp Phe Ser Ser Gly
            325                 330                 335
Asp Gly Ser Asn Phe Cys Thr Gln Trp Gly Asn Pro Glu Gln Glu Ala
            340                 345                 350
Asn Ser Arg Gly Arg Gly Arg Val Ile Glu Asp Ala Glu Glu Arg Pro
            355                 360                 365
His Ser Arg Tyr Leu Arg Arg Ala His Ser Ser Asp Arg Ala Ser Pro
            370                 375                 380
Ser Asn Gln Ser Arg Ala Lys Thr Tyr Ser Val Glu Arg Cys His Ser
385                 390                 395                 400
Val Glu Met Leu Ser Lys Pro Arg Arg Ser Leu Asp Glu Asn Gln His
            405                 410                 415
Arg Tyr Ser Pro Thr Lys Ser Asn Val Asn Val Leu Thr Ser Leu Asn
            420                 425                 430
Thr Lys Gln Pro Ile Val Lys Asp Leu Leu Lys Asp Arg Ile Met Thr
            435                 440                 445
Glu Gln Tyr Lys Asp Asn Leu Leu Asn Leu Leu Asn Lys Phe Asp Arg
450                 455                 460
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single (D) TOPOLOGY: linear (ii) MOLECULE TYPE: peptide (vi) ORIGINAL SOURCE:
    (A) ORGANISM: Mus musculus (xi) SEQUENCE DESCRIPTION: SEQ ID NO:7:

Asp Leu Thr Leu Ser Asn
1            5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Mus musculus (xi) SEQUENCE DESCRIPTION: SEQ ID NO:8:

Gly Thr Pro Asn Tyr Ile Ser Pro Glu
1            5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Mus musculus (xi) SEQUENCE DESCRIPTION: SEQ ID NO:9:

Gly Thr Xaa Xaa Tyr Xaa Ala Pro Glu
1            5

(2) INFORMATION FOR SEQ ID NO:10:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Homo sapiens (xi) SEQUENCE DESCRIPTION: SEQ ID NO:10:

Ile Gly Glu Arg Ile Glu Asp Phe Lys Val Gly Asn Leu Leu Gly Lys
1        5          10          15

Gly Ser Phe Ala Gly Val Tyr Arg Ala Glu Ser Ile His Thr Gly Leu
         20            25            30

Glu Val Ala Ile Lys Met Ile Asp Lys Lys Ala Met Tyr Lys Ala Gly
     35            40            45

Met Val Gln Arg Val Gln Asn Glu Val Lys Ile His Cys Gln Leu Lys
50               55            60

His Pro Ser Val Leu Glu Leu Tyr Asn Tyr Phe Glu Asp Asn Asn Tyr
65              70           75           80

```
                Val Tyr Leu Val Leu Glu Met Cys His Asn Gly Glu Met Asn Arg Tyr
                                85                  90                  95

Leu Lys Asn Arg Met Lys Pro Phe Ser Glu Arg Glu Ala Arg His Phe
                            100                 105                 110

Met His Gln Ile Ile Thr Gly Met Leu Tyr Leu His Ser His Gly Ile
                        115                 120                 125

Leu His Arg Asp Leu Thr Leu Ser Asn Ile Leu Leu Thr Arg Asn Met
                    130                 135                 140

Asn Ile Lys Ile Ala Asp Phe Gly Leu Ala Thr Gln Leu Asn Met Pro
                145                 150                 155                 160

His Glu Lys His Tyr Thr Leu Cys Gly Thr Pro Asn Tyr Ile Ser Pro
                                165                 170                 175

Glu Ile Ala Thr Arg Ser Ala His Gly Leu Glu Ser Asp Ile Trp Ser
                            180                 185                 190

Leu Gly Cys Met Ser Tyr Thr Leu Leu Ile Gly Arg Pro Pro Phe Asp
                        195                 200                 205

Thr Asp Thr Val Lys Asn Thr Leu Asn Lys Val Val Leu Ala Asp Tyr
                    210                 215                 220

Glu Met Pro Ala Phe Leu Ser Arg Glu Ala Gln Asp Leu Ile His Gln
                225                 230                 235                 240

Leu Leu Arg Arg Asn Pro Ala Asp Arg Leu Ser Leu Ser Ser Val Leu
                                245                 250                 255

Asp His Pro Phe Met Ser Arg Asn Pro Ser Pro Lys Ser Lys Asp Val
                            260                 265                 270

Gly (2) INFORMATION FOR SEQ ID NO:11:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Drosophila melanogaster (xi) SEQUENCE DESCRIPTION: SEQ ID NO:11:

Ile Asn Gln Arg Lys Thr Tyr Lys Arg Met Arg Phe Phe Gly Lys Gly
                1               5                   10                  15

Gly Phe Ala Lys Cys Tyr Glu Ile Ile Asp Val Glu Thr Asp Asp Val
                            20                  25                  30

Phe Ala Gly Lys Ile Val Ser Lys Lys Leu Met Ile Lys His Asn Gln
                        35                  40                  45

Lys Glu Lys Thr Ala Gln Glu Ile Thr Ile His Arg Ser Leu Asn His
                    50                  55                  60

Pro Asn Ile Val Lys Phe His Asn Tyr Phe Glu Asp Ser Gln Asn Ile
                65                  70                  75                  80

Tyr Ile Val Leu Glu Leu Cys Lys Lys Arg Ser Met Met Glu Leu His
                                85                  90                  95

Lys Arg Arg Lys Ser Ile Thr Glu Phe Glu Cys Arg Tyr Tyr Ile Tyr
                            100                 105                 110

Gln Ile Ile Gln Gly Val Lys Tyr Leu His Asp Asn Arg Ile Ile His
                        115                 120                 125

Arg Asp Leu Lys Leu Gly Asn Leu Phe Leu Asn Asp Leu Leu His Val
```

```
                130                 135                 140
    Lys Ile Gly Asp Phe Gly Leu Ala Thr Arg Ile Glu Tyr Glu Gly Glu
    145                 150                 155                 160

Arg Lys Lys Thr Leu Cys Gly Thr Ala Asn Tyr Ile Ala Pro Glu Ile
                    165                 170                 175

Leu Thr Lys Lys Gly His Ser Phe Glu Val Asp Ile Trp Ser Ile Gly
                    180                 185                 190

Cys Val Met Tyr Thr Leu Leu Val Gly Gln Pro Pro Phe Glu Thr Lys
                195                 200                 205

Thr Leu Lys Asp Thr Tyr Ser Lys Ile Lys Lys Cys Glu Tyr Arg Val
            210                 215                 220

Pro Ser Tyr Leu Arg Lys Pro Ala Ala Asp Met Val Ile Ala Met Leu
    225                 230                 235                 240

Gln Pro Asn Pro Glu Ser Arg Pro Ala Ile Gly Gln Leu Leu Asn Phe
                    245                 250                 255

Glu Phe Leu Lys Gly Ser Lys Val Pro Met Phe Leu Pro Ser Ser
                    260                 265                 270
```

(2) INFORMATION FOR SEQ ID NO:12:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mus musculus (xi) SEQUENCE DESCRIPTION: SEQ ID NO:12:

```
    Asp Pro Thr Thr Gly Lys Arg Tyr Cys Arg Gly Lys Val Leu Gly Lys
    1               5                   10                  15

Gly Gly Phe Ala Lys Cys Tyr Glu Met Thr Asp Leu Thr Asn Asn Lys
                    20                  25                  30

Val Tyr Ala Ala Lys Ile Ile Pro His Ser Arg Val Ala Lys Pro His
                35                  40                  45

Gln Arg Glu Lys Ile Asp Lys Glu Ile Glu Leu His Arg Leu Leu His
    50                  55                  60

His Lys His Val Val Gln Phe Tyr His Tyr Phe Glu Asp Lys Glu Asn
    65                  70                  75                  80

Ile Tyr Ile Leu Leu Glu Tyr Cys Ser Arg Arg Ser Met Ala His Ile
                    85                  90                  95

Leu Lys Ala Arg Lys Val Leu Thr Glu Pro Glu Val Arg Tyr Tyr Leu
                    100                 105                 110

Arg Gln Ile Val Ser Gly Leu Lys Tyr Leu His Glu Gln Glu Ile Leu
                    115                 120                 125

His Arg Asp Leu Lys Leu Gly Asn Phe Phe Ile Asn Glu Ala Met Glu
        130                 135                 140

Leu Lys Val Gly Asp Phe Gly Leu Ala Ala Arg Leu Glu Pro Leu Glu
    145                 150                 155                 160

His Arg Arg Arg Thr Ile Cys Gly Thr Pro Asn Tyr Leu Ser Pro Glu
                    165                 170                 175

Val Leu Asn Lys Gln Gly His Gly Cys Glu Ser Asp Ile Trp Ala Leu
                    180                 185                 190

Gly Cys Val Met Tyr Thr Met Leu Leu Gly Arg Pro Pro Phe Glu Thr
                    195                 200                 205
```

```
    Thr Asn Leu Lys Glu Thr Tyr Arg Cys Ile Arg Glu Ala Arg Tyr Thr
        210                 215                 220

Met Pro Ser Ser Leu Leu Ala Pro Ala Lys His Leu Ile Ala Ser Met
    225                 230                 235                 240

Leu Ser Lys Asn Pro Glu Asp Arg Pro Ser Leu Asp Asp Ile Ile Arg
                    245                 250                 255

His Asp Phe Phe Leu Gln Gly Phe Thr Pro Asp Arg Leu Ser Ser Ser
                260                 265                 270
```

(2) INFORMATION FOR SEQ ID NO:13:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Saccharomyces cerevisiae (xi) SEQUENCE DESCRIPTION: SEQ ID NO:13:

```
    Ile Lys Thr Arg Gly Lys Asp Tyr His Arg Gly His Phe Leu Gly Glu
    1               5                   10                  15

Gly Gly Phe Ala Arg Cys Phe Gln Ile Lys Asp Asp Ser Gly Glu Ile
                    20                  25                  30

Phe Ala Ala Lys Thr Val Ala Lys Ala Ser Ile Lys Ser Glu Lys Thr
                35                  40                  45

Arg Lys Lys Leu Leu Ser Glu Ile Gln Ile His Lys Ser Met Ser His
    50                  55                  60

Pro Asn Ile Val Gln Phe Ile Asp Cys Phe Glu Asp Asp Ser Asn Val
    65                  70                  75                  80

Tyr Ile Leu Leu Glu Ile Cys Pro Asn Gly Ser Leu Met Glu Leu Leu
                    85                  90                  95

Lys Arg Arg Lys Val Leu Thr Glu Pro Glu Val Arg Phe Phe Thr Thr
                    100                 105                 110

Gln Ile Cys Gly Ala Ile Lys Tyr Met His Ser Arg Arg Val Ile His
                115                 120                 125

Arg Asp Leu Lys Leu Gly Asn Ile Phe Phe Asp Ser Asn Tyr Asn Leu
    130                 135                 140

Lys Ile Gly Asp Phe Gly Leu Ala Ala Val Leu Ala Asn Glu Ser Glu
    145                 150                 155                 160

Arg Lys Tyr Thr Ile Cys Gly Thr Pro Asn Tyr Ile Ala Pro Glu Val
                    165                 170                 175

Leu Met Gly Lys His Ser Gly His Ser Phe Glu Val Asp Ile Trp Ser
                180                 185                 190

Leu Gly Val Met Leu Tyr Ala Leu Leu Ile Gly Lys Pro Pro Phe Gln
                    195                 200                 205

Ala Arg Asp Val Asn Thr Ile Tyr Glu Arg Ile Lys Cys Arg Asp Phe
    210                 215                 220

Ser Phe Pro Arg Asp Lys Pro Ile Ser Asp Glu Gly Lys Ile Leu Ile
    225                 230                 235                 240

Arg Asp Ile Leu Ser Leu Asp Pro Ile Glu Arg Pro Ser Leu Thr Glu
                    245                 250                 255

Ile Met Asp Tyr Val Trp Phe Arg Gly Thr Phe Pro Pro Ser Ile Pro
                260                 265                 270
```

```
        Ser Thr Val
                275

(2) INFORMATION FOR SEQ ID NO:14:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mus musculus (xi) SEQUENCE DESCRIPTION: SEQ ID NO:14:

Asp Pro Arg Ser Arg Arg Gln Tyr Ile Arg Gly Arg Phe Leu Gly Lys
    1               5                   10                  15

Gly Gly Phe Ala Lys Cys Phe Glu Ile Ser Asp Ala Asp Thr Lys Glu
                    20                  25                  30

Val Phe Ala Gly Lys Ile Val Pro Lys Ser Leu Leu Leu Lys Pro His
                    35                  40                  45

Gln Lys Glu Lys Met Ser Met Glu Ile Ser Ile His Arg Ser Leu Ala
                50                  55                  60

His Gln His Val Val Gly Phe His Asp Phe Glu Asp Ser Asp Phe
    65                  70                  75                  80

Val Phe Val Val Leu Glu Leu Cys Arg Arg Arg Ser Leu Leu Glu Leu
                    85                  90                  95

His Lys Arg Arg Lys Ala Leu Thr Glu Pro Glu Ala Arg Tyr Tyr Leu
                    100                 105                 110

Arg Gln Ile Val Leu Gly Cys Gln Tyr Leu His Arg Asn Gln Val Ile
                115                 120                 125

His Arg Asp Leu Lys Leu Gly Asn Leu Phe Leu Asn Glu Asp Leu Glu
                130                 135                 140

Val Lys Ile Gly Asp Phe Gly Leu Ala Thr Lys Val Glu Tyr Glu Gly
    145                 150                 155                 160

Glu Arg Lys Lys Thr Leu Cys Gly Thr Pro Asn Tyr Ile Ala Pro Glu
                    165                 170                 175

Val Leu Ser Lys Lys Gly His Ser Phe Glu Val Asp Val Trp Ser Ile
                    180                 185                 190

Gly Cys Ile Met Tyr Thr Leu Leu Val Gly Lys Pro Pro Phe Glu Thr
                    195                 200                 205

Ser Cys Leu Lys Glu Thr Tyr Leu Arg Ile Lys Lys Asn Glu Tyr Ser
                    210                 215                 220

Ile Pro Lys His Ile Asn Pro Val Ala Ala Ser Leu Ile Gln Lys Met
    225                 230                 235                 240

Leu Gln Thr Asp Pro Thr Ala Arg Pro Thr Ile His Glu Leu Leu Asn
                    245                 250                 255

Asp Glu Phe Phe Thr Ser Gly Tyr Ile Pro Ala Arg Leu Pro Ile Thr
                    260                 265                 270
```